United States Patent [19]

Gardlik et al.

[11] Patent Number: 5,234,610
[45] Date of Patent: Aug. 10, 1993

[54] TREATMENT OF FABRIC WITH PERFUME/CYCLODEXTRIN COMPLEXES

[75] Inventors: John M. Gardlik, Cincinnati; Toan Trinh, Maineville; Todd J. Banks, West Chester; Fernando Benvegnu, Maineville, all of Ohio

[73] Assignee: The Procter & Gamble Company, Cincinnati, Ohio

[21] Appl. No.: 809,184

[22] Filed: Dec. 17, 1991

Related U.S. Application Data

[62] Division of Ser. No. 337,036, Apr. 12, 1989, Pat. No. 5,102,564.

[51] Int. Cl.$^5$ .................... D06M 13/00; C11D 3/50
[52] U.S. Cl. .................................. 252/8.6; 252/8.75; 252/8.8; 252/174.11
[58] Field of Search ............. 252/8.6, 8.75, 8.8, 252/113, 174.11, 131, 528, 546, 547

[56] References Cited

U.S. PATENT DOCUMENTS

| | | | |
|---|---|---|---|
| 3,442,692 | 5/1969 | Gaiser | 252/8.6 |
| 4,073,996 | 2/1978 | Bedenk et al. | 428/274 |
| 4,267,166 | 5/1981 | Yajima | 424/48 |
| 4,296,138 | 10/1981 | Boden | 426/534 |
| 4,348,416 | 9/1982 | Boden | 426/3 |
| 4,678,598 | 7/1987 | Ogino et al. | 252/174.17 |
| 4,992,198 | 2/1991 | Nebashi et al. | 252/174.11 |

FOREIGN PATENT DOCUMENTS

0041328  12/1981  European Pat. Off. .
3020269   1/1981  Fed. Rep. of Germany .
63-165498 7/1988  Japan .

Primary Examiner—Prince Willis, Jr.
Attorney, Agent, or Firm—Robert B. Aylor

[57] ABSTRACT

An effective amount of perfume/cyclodextrin complex is applied to fabric that is preferably at least partially wetted. A preferred method applies said complex to said fabric in an automatic laundry dryer. The perfume/cyclodextrin complexes are preferably incorporated into solid, dryer-activated, fabric treatment (conditioning) compositions, preferably containing fabric softeners, more preferably cationic and/or nonionic fabric softeners. The complexes provide fabrics with perfume benefits when they are rewetted after drying. Volatile perfume materials, including those materials that are commonly associated with "freshness" can be applied to the fabrics in an effective way. Clay provides protection for said perfume/cyclodextrin complexes, especially when certain materials like some nonionic fabric softeners and/or fatty acids are present and in contact with said perfume/cyclodextrin complexes.

35 Claims, No Drawings

TREATMENT OF FABRIC WITH PERFUME/CYCLODEXTRIN COMPLEXES

This is a division of application Ser. No. 07/337,036, filed on Apr. 12, 1989 now U.S. Pat. No. 5,102,564.

TECHNICAL FIELD

The present invention relates to an improvement in fabric treatment with perfumes and compositions and products for accomplishing said treatment, said products, and/or compositions, being, preferably, either in particulate form or attached to a substrate.

BACKGROUND OF THE INVENTION

The use of perfumes in solid, dryer-activated, fabric conditioning products is disclosed in many patents including U.S. Pat. No. 4,808,086 of Mark D. Evans, Gregory B. Huntington, Robert L. Stewart, Peter H. Wolf, and Roger E. Zimmerer for "ARTICLES AND METHODS FOR TREATING FABRICS," issued Feb. 28, 1989, said patent being incorporated herein by reference. There has been a continuing need for improved deposition and longevity of perfume.

SUMMARY OF THE INVENTION

It has now been discovered that perfumes can be used for fabric treatment (conditioning), either alone or in, e.g., softening, compositions, including those softening compositions that are detergent compatible, by forming complexes of the perfumes with cyclodextrins and/or their derivatives as described hereinafter. These complexes have been disclosed generically and have been suggested for use in a variety of products. However, their application to fabrics, especially in a laundry dryer, either alone or in solid, dryer-activated, fabric conditioning compositions, has not been disclosed. These complexes provide a remarkable and totally unexpected effect. Specifically, the cyclo-dextrin/perfume complexes provide improved perfume deposition on fabric, especially of volatile perfume materials, and delayed and/or controlled release when the fabrics are wetted or rewetted.

Thus, in its broadest aspects, the invention relates to the method of applying an effective amount of perfume/cyclodextrin complex to fabric. Preferably the fabric is at least partially wetted (damp) and more preferably the method is carried out in an automatic laundry dryer.

DESCRIPTION OF THE INVENTION

Perfume/cyclodextrin complexes can be applied directly to fabrics, preferably in automatic laundry dryers, and/or preferably in particulate form, and/or preferably when the fabrics are at least partially wet. Surprisingly, the complexes are effectively attached to fabrics of all common types. The strength of the attachment is such that the application can occur in an automatic laundry dryer to achieve good distribution despite the violent agitation of the fabrics in the dryer and the effect of the heated drying air passing over the surface of the fabrics at high speeds. Alternatively, the complexes can be applied directly to fabric by spraying a suspension of complex in a solvent that will not displace the perfume from the complex or by "dusting" to achieve good distribution. E.g., the perfume/cyclodextrin particles can be sprayed and/or shaken onto the fabric, preferably damp fabric. Propellants or air under pressure can be used to form the dispersion. The complexes release some of the perfume when there is water in the fabric, but, surprisingly, a large amount of perfume remains in the complexes attached to the fabric. When the fabric is subsequently rewetted, additional perfume is released to provide an odor effect. Such odor effects are highly desirable both to generate pleasant odors when the fabric is rewetted, e.g., for towels and/or washcloths, and to cover undesirable odors such as those associated with perspiration. The odor effects on rewetting also serve as an effective pleasant signal that the fabric is becoming soiled while providing pleasant freshness effects until the soiled fabric can be exchanged for clean fabric. Thus it is esssential that at least an effective amount be attached to the fabric. Effective amounts are typically in the range of from about 0.005 g to about 5g, preferably from about 0.01 g to about 1 g, more preferably from about 0.05 g to about 0.5 g per kg of fabric. The wetter the fabric, the more perfume is released initially, and more of the remaining complex is effectively attached to the fabric. When the fabric is almost dry, little complex is destroyed and less perfume is applied initially, but the fabric exhibits odor effects upon rewetting.

More preferably, the perfume/cyclodextrin complex is provided as part of a dryer-activated, fabric conditioning composition as described hereinafter. Such compositions provide a convenient way to introduce the perfume/cyclodextrin complex into the dryer. In the case of detergent-compatible fabric conditioning compositions, as described hereinafter, the composition also permits the perfume/cyclodextrin complex to survive the wash/rinse portions of the laundry process and reach the dryer with the complex still present in an effective amount. Without protection, the perfume is released from the complex by the action of water in the wash and/or rinse cycles.

1. THE FABRIC CONDITIONING COMPOSITIONS

The present invention also relates to improved solid, dryer-activated, fabric conditioning compositions which are either (A) incorporated into articles of manufacture in which the fabric conditioning compositions are, e.g., on a substrate, or, are (B) detergent-compatible compositions, typically in the form of particles.

A. Substrate Articles

In preferred embodiments, the present invention encompasses articles of manufacture, adapted for use to provide unique perfume benefits and to soften fabrics in an automatic laundry dryer, of the types disclosed in U.S. Pat. Nos: 3,989,631 Marsan, issued Nov. 2, 1976; 4,055,248, Marsan, issued Oct. 25, 1977; 4,073,996, Bedenk et al., issued Feb. 14, 1978; 4,022,938, Zaki et al., issued May 10, 1977; 4,764,289, Trinh, issued Aug. 16, 1988; 4,808,086, Evans et al., issued Feb. 28,1989; 4,103,047, Zaki et al., issued Jul. 25, 1978; 3,736,668, Dillarstone, issued Jun. 5, 1973; 3,701,202, Compa et al., issued Oct. 31,1972; 3,634,947, Furgal, issued Jan. 18, 1972; 3,633,538, Hoeflin, issued Jan. 11, 1972; and 3,435,537, Rumsey, issued Apr. 1, 1969; and 4,000,340, Murphy et al., issued Dec. 28, 1976, all of said patents being incorporated herein by reference.

Typical articles of manufacture of this type include articles comprising:

I. a fabric conditioning composition comprising:

i. from about 30% to about 99% of fabric softening agent; and ii. an effective amount, preferably from about 0.5% to about 60%, of perfume/cyclodextrin complex, as described hereinafter;

II. a dispensing means which provides for release of an effective amount of said composition to fabrics in an automatic laundry dryer at automatic laundry dryer operating temperatures, e.g., from about 35° C. to 115° C.

When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1. The invention also comprises the method of manufacturing such an article of manufacture utilizing said complex ii., either by application of the complex ii. directly to said dispensing means II, or by premixing the complex ii. with the fabric softening agent i. The softener helps protect the complex from the water in the environment which is desirable. However, separate application of complex to said substrate is also possible and can diminish interaction of softener ingredients with the perfume.

The term "fabric softening agent" as used herein includes cationic and nonionic fabric softeners used alone and also in combination with each other. A preferred fabric softening agent of the present invention is a mixture of cationic and nonionic fabric softeners.

(1) Fabric Softening Agents

Examples of fabric softening agents that are especially useful in the substrate articles are the compositions described in U.S. Pat. Nos. 4,103,047, Zaki et al., issued Jul. 25, 1978; 4,237,155, Kardouche, issued Dec. 2, 1980; 3,686,025, Morton, issued Aug. 22, 1972; 3,849,435, Diery et al., issued Nov. 19, 1974; and U.S. Pat. No. 4,037,996, Bedenk, issued Feb. 14, 1978; said patents are hereby incorporated herein by reference. Other fabric softening agents are disclosed hereinafter with respect to detergent-compatible fabric conditioning compositions.

Particularly preferred cationic fabric softeners for substrate articles include quaternary ammonium salts such as dialkyl dimethylammonium chlorides, methylsulfates and ethylsulfates wherein the alkyl groups can be the same or different and contain from about 14 to about 22 carbon atoms. Examples of such preferred materials include ditallowalkyldimethylammonium methylsulfate (DTDMAMS), distearyldimethylammonium methylsulfate, dipalmityldimethylammonium methylsulfate and dibehenyldimethylammonium methylsulfate. Also particularly preferred are the carboxylic acid salts of tertiary alkylamines disclosed in said Kardouche patent. Examples include stearyldimethylammonium stearate, distearylmethylammonium myristate, stearyldimethylammonium palmitate, distearylmethylammonium palmitate, and distearylmethylammonium laurate. These carboxylic salts can be made in situ by mixing the corresponding amine and carboxylic acid in the molten fabric conditioning composition.

Another preferred type of fabric softener is described in detail in U.S. Pat. No. 4,661,269, Toan Trinh, Errol H. Wahl, Donald M. Swartley and Ronald L. Hemingway, issued Apr. 28, 1987, said patent being incorporated herein by reference.

Examples of nonionic fabric softeners are the sorbitan esters, $C_{12}$–$C_{26}$ fatty alcohols, and fatty amines described herein.

A preferred fabric softening agent for use in substrate articles comprises a mixture of (1) $C_{10}$–$C_{26}$ acyl sorbitan esters and mixtures thereof, (2) quaternary ammonium salt, and (3) tertiary alkylamine. The quaternary ammonium salt is preferably present at a level of from about 5% to about 25%, more preferably from about 7% to about 20% of the fabric conditioning composition. The sorbitan ester is preferably present at a level of from about 10% to about 50%, more preferably from about 20% to about 40%, by weight of the fabric conditioning composition. The tertiary alkylamine is present at a level of from about 5% to about 25%, more preferably from 7% to about 20% by weight of the fabric conditioning composition. The preferred sorbitan ester comprises a member selected from the group consisting of $C_{10}$–$C_{26}$ acyl sorbitan monoesters and $C_{10}$–$C_{26}$ acyl sorbitan di-esters, and ethoxylates of said esters wherein one or more of the unesterified hydroxyl groups in said esters contain from 1 to about 6 oxyethylene units, and mixtures thereof. The quaternary ammonium salt is preferably in the methylsulfate form. The preferred tertiary alkylamine is selected from the group consisting of alkyldimethylamine and dialkylmethylamine and mixtures thereof, wherein the alkyl groups can be the same or different and contain from about 14 to about 22 carbon atoms.

Yet another preferred fabric softening agent comprises a carboxylic acid salt of a tertiary alkylamine, in combination with a fatty alcohol and a quaternary ammonium salt. The carboxylic acid salt of a tertiary amine is used in the fabric conditioning composition preferably at a level of from about 5% to about 50%, and more preferably, from about 15% to about 35%, by weight of the fabric treatment composition. The quaternary ammonium salt is used preferably at a level of from about 5% to about 25%, and more preferably, from about 7% to about 20%, by weight of the fabric treatment composition. The fatty alcohol can be used preferably at a level of from about 10% to about 25%, and more preferably from about 10% to about 20%, by weight of the fabric treatment composition. The preferred quaternary ammonium salt is selected from the group consisting of dialkyl dimethylammonium salt wherein the alkyl groups can be the same or different and contain from about 14 to about 22 carbon atoms and wherein the counteranion is selected from the group consisting of chloride, methylsulfate and ethylsulfate, preferably methylsulfate. The preferred carboxylic acid salt of a tertiary alkylamine is selected from the group consisting of fatty acid salts of alkyldimethylamines wherein the alkyl group contains from about 14 to about 22 carbon atoms, and the fatty acid contains from about 14 to about 22 carbon atoms, and mixtures thereof. The preferred fatty alcohol contains from about 14 to about 22 carbon atoms.

More biodegradable fabric softener compounds can be desirable. Biodegradability can be increased, e.g., by incorporating easily destroyed linkages into hydrophobic groups. Such linkages include ester linkages, amide linkages, and linkages containing unsaturation and/or hydroxy groups. Examples of such fabric softeners can be found in U.S. Pat. Nos. 3,408,361, Mannheimer, issued Oct. 29, 1968; 4,709,045, Kubo et al., issued Nov. 24, 1987; 4,233,451, Pracht et al., issued Nov. 11, 1980; 4,127,489, Pracht et al., issued Nov. 28, 1979; 3,689,424, Berg et al., issued Sept. 5, 1972; 4,128,485, Baumann et al., issued Dec. 5, 1978; 4,161,604, Elster et al., issued Jul. 17, 1979; 4,189,593, Wechsler et al., issued Feb. 19, 1980; and 4,339,391, Hoffman et al., issued Jul. 13, 1982, said patents being incorporated herein by reference.

A preferred article of the present invention includes a fabric treatment composition which comprises from about 0.5% to about 60%, preferably from about 1% to about 50%, more preferably from about 5% to about 40%, of perfume/cyclodextrin complex and from about 30% to about 99%, preferably from about 40% to about 90%, of fabric conditioning (softening) agent. Preferably, said fabric softening agent is selected from cationic and nonionic fabric softeners and mixtures thereof. Preferably, said fabric softening agent comprises a mixture of about 5% to about 80% of a cationic fabric softener and about 10% to about 85% of a nonionic fabric softener by weight of said fabric treatment composition. The selection of the components is such that the resulting fabric treatment composition has a melting point above about 38° C. and is flowable at dryer operating temperatures.

It is desirable, for ease of application, to intimately admix the ingredients of the fabric treatment before use and before application to a substrate dispensing means. This can be accomplished by premixing the ingredients by co-melting, co-milling, etc., or by combinations of such techniques. For processing reasons, it is desirable to have a clay in the fabric softener composition in accordance with the teachings found in the patents incorporated by reference hereinbefore, and especially U.S. Pat. No. 4,073,996. As discussed hereinafter, clay provides special benefits in the context of the present invention.

(2) Dispensing Means

In the preferred substrate article embodiment, the fabric treatment compositions are provided as an article of manufacture in combination with a dispensing means such as a flexible substrate which effectively releases the composition in an automatic laundry (clothes) dryer. Such dispensing means can be designed for single usage or for multiple uses. The dispensing means can also be a "carrier material" that releases the fabric softener composition and then is dispersed and/or exhausted from the dryer.

The dispensing means will normally carry an effective amount of fabric treatment composition. Such effective amount typically provides sufficient fabric conditioning agent and/or anionic polymeric soil release agent for at least one treatment of a minimum load in an automatic laundry dryer. Amounts of fabric treatment composition for multiple uses, e.g., up to about 30, can be used. Typical amounts for a single article can vary from about 0.25 g to about 100 g, preferably from about 0.5 g to about 10 g, most preferably from about 1 g to about 5 g.

One such article comprises a sponge material releasably enclosing enough fabric treatment composition to effectively impart fabric soil release and softness benefits during several cycles of clothes. This multi-use article can be made by filling a hollow sponge with about 20 grams of the fabric treatment composition.

Other devices and articles suitable for dispensing the fabric treatment composition into automatic dryers include those described in U.S. Pat. Nos. 4,103,047, Zaki et al., issued Jul. 25, 1978; 3,736,668, Dillarstone, issued June 5, 1973; 3,701,202, Compa et al., issued Oct. 31, 1972; 3,634,947, Furgal, issued Jan. 18, 1972; 3,633,538, Hoeflin, issued Jan. 11, 1972; and 3,435,537, Rumsey, issued Apr. 1, 1969. All of these patents are incorporated herein by reference.

A highly preferred article herein comprises the fabric treatment composition releasably affixed to a flexible substrate in a sheet configuration. Highly preferred paper, woven or nonwoven "absorbent" substrates useful herein are fully disclosed in Morton, U.S. Pat. No. 3,686,025, issued Aug. 22, 1972, incorporated herein by reference. It is known that most substances are able to absorb a liquid substance to some degree; however, the term "absorbent" as used herein, is intended to mean a substance with an absorbent capacity (i.e., a parameter representing a substrates ability to take up and retain a liquid) from 4 to 12, preferably 5 to 7, times its weight of water.

Determination of absorbent capacity values is made by using the capacity testing procedures described in U.S. Federal Specifications UU-T-595b, modified as follows:

1. tap water is used instead of distilled water;
2. the specimen is immersed for 30 seconds instead of 3 minutes;
3. draining time is 15 seconds instead of 1 minute; and
4. the specimen is immediately weighed on a torsion balance having a pan with turned-up edges.

Absorbent capacity values are then calculated in accordance with the formula given in said Specification. Based on this test, one-ply, dense bleached paper (e.g., kraft or bond having a basis weight of about 32 pounds per 3,000 square feet) has an absorbent capacity of 3.5 to 4, commercially available household one-ply toweling paper has a value of 5 to 6; and commercially available two-ply household toweling paper has a value of 7 to about 9.5.

Using a substrate with an absorbent capacity of less than 4 tends to cause too rapid release of the fabric treatment composition from the substrate resulting in several disadvantages, one of which is uneven conditioning of the fabrics. Using a substrate with an absorbent capacity over 12 is undesirable, inasmuch as too little of the fabric treatment composition is released to condition the fabrics in optimal fashion during a normal drying cycle.

Such a substrate comprises a nonwoven cloth having an absorbent capacity of preferably from about 5 to 7 and wherein the weight ratio of fabric treatment composition to substrate on a dry weight basis ranges from about 5:1 to 1:1.

Nonwoven cloth substrates preferably comprise cellulosic fibers having a length of from 3/16 inch to 2 inches and a denier of from 1.5 to 5 and the substrates are adhesively bonded together with binder resin.

The flexible substrate preferably has openings sufficient in size and number to reduce restriction by said article of the flow of air through an automatic laundry dryer. The better openings comprise a plurality of rectilinear slits extended along one dimension of the substrate.

(3) Usage

The method aspect of the substrate embodiment of this invention for imparting the above-described fabric treatment composition to fabric to provide perfume effects and/or softening and/or antistatic effects to fabric in an automatic laundry dryer comprises: commingling pieces of damp fabric by tumbling said fabric under heat in an automatic clothes dryer with an effective amount of the fabric treatment composition, at least the continuous phase of said composition having a melting point greater than about 35° C. and said composition being mobilized, e.g., flowable, at dryer operating temperature, said composition comprising from about 0.5% to about 60%, preferably from about 1% about 50%, more preferably from about 5% to about 40%, of perfume/cyclodextrin complex and from about 30% to about 99%, preferably from about 40% to about 90%, of fabric softening agent selected from the above-defined cationic and nonionic fabric softeners and mixtures thereof.

The method herein is carried out in the following manner. Damp fabrics, usually containing from about 1 to about 3.5 times their weight of water, are placed in the drum of an automatic laundry (clothes) dryer. In practice, such damp fabrics are commonly obtained by laundering, rinsing and spin-drying the fabrics in a standard washing machine. In a preferred mode, the present process is carried out by fashioning an article comprising the substrate-like dispensing means of the type hereinabove described in releasable combination with a fabric treatment composition. This article is simply added to a clothes dryer together with the damp fabrics to be treated. The dryer is then operated in standard fashion to dry the fabrics, usually at a temperature of from about 50° C. to about 80°O C. for a period from about 10 minutes to about 60 minutes, depending on the fabric load and type. On removal from the dryer, the dried fabrics have acquired improved perfume benefits and are softened.

After one treatment in an automatic clothes dryer with an article of the present invention, the fabrics will have acquired a noticeable perfume benefit. I.e., more perfume is deposited in the form of perfume/cyclodextrin complex and, when the fabrics are rewetted, they will exhibit noticeable perfume odor.

B. Detergent-Compatible Compositions

The other type of fabric conditioning composition useful herein is detergent-compatible and includes compositions containing softening particles such as those known in the art, including specifically: U.S. Pat. No. 3,936,537, Baskerville Jr., issued Feb. 3, 1976, and U.S. Pat. No. 4,095,946, Jones, issued Jun. 20, 1978, both of which teach the use of intimate mixtures of organic dispersion inhibitors (e.g., stearyl alcohol and fatty sorbitan esters) with solid fabric softener to improve the survival of the softener in the presence of detergent in the washer so that the softener can act on the fabrics when it is mobilized in the dryer, and U.S. Pat. No. 4,234,627, Schilling, issued Nov. 18, 1980, which teaches microencapsulation of fabric softener (The microcapsules survive the wash and adhere to the fabric surface. They are then ruptured by subsequent tumbling of the fabric in the dryer, thereby releasing softener to the fabrics.)

The particles in such detergent-compatible fabric conditioning compositions comprise at least about 10% of fabric softening agent, preferably cationic fabric softening agent. For detergent compatibility, the particles often have a coating as described hereinafter, a sufficiently large particle size (e.g., a minimum dimension greater than about 5,000 microns), or some combination of coating and particle size depending upon the identity of the softener, the other materials in the fabric softening composition, etc.

The detergent-compatible fabric conditioning composition particles of the present invention typically comprise an inner core of a fabric conditioning composition which usually comprises a cationic fabric softening agent, and, if necessary, an outer coating which protects the inner core, preferably one which completely surrounds the core and comprises a substantially water-insoluble material having a melting point above about 35° C., preferably above about 50° C. By "substantially water-insoluble" herein is meant having a solubility in 35° C. water of less than about 50 ppm. The particles have diameters of from about 5 microns to about 15,000 microns, preferably greater than about 300 microns, and most preferably greater than about 500 microns, with a number average of from about 600 to about 9,000 microns. The particles typically will be of a generally spherical shape, but can also have an irregular shape. The particle sizes quoted herein refer to the largest dimension (diameter or length) of the particle unless otherwise stated.

The larger, uncoated particles having no dimension less than about 5,000 microns, preferably 10,000 microns, are compatible with detergent compositions even if uncoated. Such particles are desirable for many reasons including ease of manufacture. Particles having dimensions that are less than about 5,000 microns require more or less coating depending on the size. Particles having maximum dimensions of more than 1,500 microns require less coating for survival. Large, "jumbo" particles are really practical only when placed in a pouch product as described hereinafter since segregation and/or loss of the particle during the laundry process are likely.

(1) The Fabric Softener

Typical cationic fabric softeners useful in the detergent-compatible fabric conditioning compositions herein include those that have been described hereinbefore with respect to the substrate articles and include quaternary ammonium salts of the formula

$[R_1R_2R_3R_4N]+Y-$ wherein one or two of $R_1$, $R_2$, $R_3$ and $R_4$ groups is an organic radical containing a group selected from a $C_{12}$–$C_{22}$ aliphatic radical or an alkylphenyl or alkylbenzyl radical having from 10 to 16 carbon atoms in the alkyl chain, the remaining groups being selected from $C_1$–$C_4$ alkyl, $C_2$–$C_4$ hydroxyalkyl and cyclic structures in which the nitrogen atom in the above formula forms part of the ring, and Y constitutes an anionic radical such as halide, nitrate, bisulfate, methylsulfate, ethylsulfate and phosphate, to balance the cationic charge.

In the context of the above definition, the hydrophobic moiety (i.e., the $C_{12}$–$C_{22}$ aliphatic, $C_{10}$–$C_{16}$ alkyl phenol or alkylbenzyl radical) in the organic radical $R_1$ or $R_2$ can be directly attached to the quaternary nitrogen atom or can be indirectly attached thereto through an amide, ester, alkoxy, ether, or like grouping.

The quaternary ammonium compounds useful in detergent compatible compositions herein include both water-soluble compounds and substantially water-insoluble compounds which are dispersible in water. For example, imidazolinium compounds of the structure

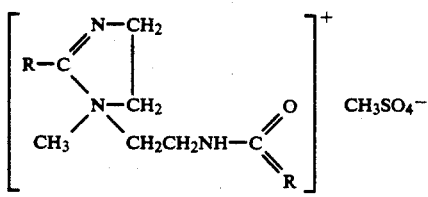

wherein R is a $C_{16}$ to $C_{22}$ alkyl group, possess appreciable water solubility, but can be utilized in the present invention.

The following are representative examples of quaternary ammonium softening compounds suitable for use in the detergent-compatible compositions of the present invention. All the quaternary ammonium compounds listed can be included in the present invention, but the compilation of suitable quaternary compounds hereinafter is only by way of example and is not intended to be limiting of such compounds. Dioctadecyldimethylammonium methylsulfate is an especially preferred fabric softening compound for use herein, by virtue of its high antistatic, as well as fabric softening activity; ditallowalkyldimethylammonium methylsulfate is equally preferred because of its ready availability and its good antistatic activity; other useful di-long chain quaternary compounds are dicetyldimethylammonium chloride, didocosyldimethylammonium chloride, didodecyldimethylammonium chloride, ditallowalkyldimethylammonium bromide, dioleoyldimethylammonium methylsulfate, ditallowalkyldiethylammonium chloride, ditallowalkyldipropylammonium bromide, ditallowalkyldibutylammonium fluoride, cetyldecylmethylethylammonium chloride, bis-[ditallowalkyldimethylammonium] bisulfate, tris-[ditallowalkyldimethylammonium] phosphate, 1-methyl-1-tallowamidoethyl-2-tallowimidazolinium methylsulfate, and the like. Particularly preferred quaternary ammonium fabric softening compounds are ditallowalkyldimethylammonium chloride (DTDMAC) and ditallowalkyldimethylammonium methylsulfate. The fabric softener core of the coated particles of the invention comprises from about 70% to about 98% and most preferably about 85% to about 97% of the particle. All percentages herein are "by weight" unless otherwise indicated.

The quaternary ammonium softener compounds used in this invention in both substrate articles and detergent-compatible compositions can be prepared in various ways well-known in the art and many such materials are commercially available. The quaternaries are often made from alkyl halide mixtures corresponding to the mixed alkyl chain lengths in fatty acids. For example, the ditallowalkyl quaternaries are made from alkyl halides having mixed $C_{14}$-$C_{18}$ chain lengths. Such mixed di-long chain quaternaries are useful herein and are preferred from a cost standpoint.

The anionic group which can be the counter-ion in the quaternary compounds useful herein is typically a halide (e.g., chloride or bromide), nitrate, bisulfate, ethylsulfate, or methylsulfate. The methylsulfate and chloride ions are the preferred counter-anions from an availability standpoint; while the methylsulfate anion is most preferred because of its minimization of corrosive effects on the automatic clothes dryers in which it is used.

The softener compositions, e.g., the core composition of the coated particles, can consist entirely of cationic fabric softeners and the silica particles described hereinafter. The softener composition, e.g., core, will generally comprise at least 10%, usually from about 10% to about 90%, preferably from about 20% to about 60%, fabric softening agent, preferably cationic fabric softener, and from about 0.5% to about 60%, preferably from about 1% to about 50%, more preferably from about 5% to about 40% of perfume-cyclodextrin complex as described hereinafter. Optionally, and preferably, the composition can contain additional materials besides the perfume/cyclodextrin complexes described hereinafter, including auxiliary fabric softening agents (e.g., smectite clay, fatty alcohols and fatty amine(s), such as ditallowmethyl amine or 1-tallowamidoethyl-2-tallowimidazoline), soil release agents, fabric brighteners, etc. Additional disclosure of materials which can be applied to fabrics along with cationic fabric softening agents in a laundry dryer and, therefore, can be part of the core composition of the particles herein, are disclosed in U.S. Pat. Nos. 4,073,996, Bedenk et al., issued Feb. 14, 1978; 4,237,155, Kardouche, issued Dec. 2, 1980; and 4,421,792, Rudy et al., issued Dec. 20, 1983, all incorporated herein by reference.

(2) The Coating Materials

The preferred coating materials used in the coated particles are substantially water-insoluble materials, typically (but not necessarily) selected from waxy materials such as paraffinic waxes, microcrystalline waxes, animal waxes, vegetable waxes, saturated fatty acids and fatty alcohols having from 12 to 40 carbon atoms in their alkyl chain, and fatty esters such as fatty acid triglycerides, fatty acid esters of sorbitan and fatty acid esters of fatty alcohols, or from substantially water-insoluble polymers. Typical specific suitable waxy coating materials include lauric, myristic, palmitic, stearic, arachidic and behenic acids, stearyl and behenyl alcohol, microcrystalline wax, beeswax, spermaceti wax, candelilla wax, sorbitan tristearate, sorbitan tetralaurate, tripalmitin, trimyristin and octacosane. A preferred waxy material is stearyl alcohol.

Examples of water-insoluble polymeric materials which can be used for the coating of the particles herein are cellulose ethers such as ethyl, propyl or butyl cellulose; cellulose esters such as cellulose acetate, propionate, butyrate or acetate-butyrate; ureaformaldehyde resins, polyvinyl chloride, polyvinylidene chloride, polyethylene, polypropylene, polyacrylates, polymethacrylates, polymethyl-methacrylates and nylon. Such materials and their equivalents are described in greater detail in any conventional handbook of synthetic organic plastics, for example, in *Modern Plastics Encyclooaedia Volume*, Vol. 62, No. 10A (for 1985-1986) at pages 768-787, published by McGraw-Hill, New York, N.Y. (October 1985), incorporated herein by reference. A preferred polymeric material is ethyl cellulose. The polymeric coating materials can be plasticized with known plasticizing agents such as phthalate, adipate and sebacate esters, polyols (e.g., ethylene glycol), tricresyl phosphate, castor oil and camphor. These polymeric coatings are preferred for the superior protection they provide.

The coating surrounds the cationic fabric softener core and is present in an amount of from about 2% to about 30%, preferably from about 3% to about 15% by weight of the particle.

The coating material can comprise a mixture of waxy coating materials and polymeric coating materials. In such mixtures the waxy coating material will typically comprise from about 70% to about 90% of the mixture and the polymeric material about 30% to about 10%.

Typically, the coating material will have a hardness which corresponds to a needle penetration value of about 0.6 mm or less, and preferably less than about 0.1 mm, as measured by ASTM Test D-1321, modified by using a 100g weight instead of a 50g weight. The test is performed at 25°-27° C. In the case of polymeric coating materials, sample preparation is accomplished by dissolving the polymer in a volatile solvent and then evaporating the solvent after the polymer solution has been placed in the test container. For waxy coating materials, sample preparation is done by melting the sample and then solidifying it in the test container in the manner set forth in the ASTM method.

The function of the coating which surrounds the fabric softener is to prevent the softener from becoming dissolved and/or dispersed in the wash water when the particles are present during the wash step of a laundry process, and thereby prevent interaction between the fabric softener and the detergent. During the washing and rinsing of the fabrics, a substantial amount of the particles adhere to, or become entrapped within folds of the fabrics. When the fabrics are dried in a heated automatic clothes dryer (typically at temperatures of about 65° to 85° C.), the coating and the fabric softener core composition melt, thereby permitting the softener to spread throughout the fabric load and soften the fabrics. The coating materials are disclosed in the copending U.S. patent application of Wierenga et al. for DETERGENT COMPATIBLE, DRYER RELEASED FABRIC SOFTENING/ANTISTATIC AGENTS, Ser. No. 058,449, filed Jun. 5, 1987.

If the softener particles will survive the conditions of use and be available in the clothes dryer, a coating is not required.

If the particles are incorporated directly into a loose granular detergent composition, it is preferred that the particle size of the softener particles be similar to the particle size of the detergent granule in order to minimize segregation. This will typically be in the range of from about 500 to about 1,500 microns. Softener particles which are smaller in size than the detergent granules can be agglomerated to form larger particles to match the particle size of the detergent granules into which they will be incorporated. The agglomeration can be accomplished by using water-soluble or dispersible materials such as polyvinyl alcohol, sodium carboxymethyl cellulose, gelatin and polyoxyethylene waxes. The agglomerates disintegrate when the detergent composition is added to water. Methods and agglomerating agents for agglomeration of fabric softener particles are described in U.S. Pat. No. 4,141,841, McDanald, issued Feb. 27, 1979, incorporated by reference herein.

Desirable additives to such detergent-compatible compositions include silica particles which have a diameter of from about 0.001 micron to about 15 microns. The silica particles, when they have a diameter of greater than about one micron and are present at a level of at least about 4% in said dryer-activated fabric softening compositions, can provide protection against staining. It is also often desirable that silica gel particles be used in softener compositions to maintain the desired viscosity range, e.g., from about 5,000 to about 30,000 mPas, preferably from about 8,000 to about 20,000 mPas, of the softener when it is in the molten form, while improving the aesthetic character of any subsequent noticeable softener deposits on fabric by acting as a visual "masking" adjuvant. The desired level of silica gel particles in solid softener compositions, including the substrate articles described hereinbefore, is from about 2% to about 15%, preferably from about 4% to about 12%. The preferred particle size that is desired for softener compositions is from about 1 micron to about 15 microns, preferably from about 2 microns to about 6 microns.

(3) Preparation of Particles

In preparing the optional coated softener particles of the invention, the solid fabric softener composition and any visual "masking" adjuvant (MA), which are to be the core of the particles, are formed into particles having a size of from about 5 microns to about 15,000 microns. This can be accomplished, for example, by milling the solid softener composition or by melting the composition, mixing the MA into the resulting melt, and spraying the melt through appropriate sized nozzles into an atmosphere having a temperature below the melting point of the softener, thereby forming the softener-composition/MA mixture into solid particles.

The particles of softener-composition/MA can then be coated with coating material which is typically either melted or dissolved in a volatile solvent. The coating can be done at a temperature which is below the melting point of the softener composition, and the coated particles are then cooled (or the solvent is evaporated) to solidify the coating. The coating is typically applied in a fluidized bed type apparatus. A suitable type of apparatus is that described in U.S. Pat. No. 3,196,827, Wurster et al., issued Jul. 27, 1965, incorporated by reference herein. In this apparatus, solid softener core particles are suspended in an air stream which carries them in a smooth cyclic flow past the coating nozzle, which sprays them with fluid coating material. Air atomizes and expels the coating fluid through the coating nozzle. The atomized coating fluid covers the surfaces of the core particles. The coated particles are lifted on the air stream and the fluid coating solidifies on the surface of the particles as the air stream lifts them away from the nozzle. The particles then settle out of the air stream and begin another cycle which takes them past the nozzle again. The process is repeated until the desired amount of coating has been deposited on the particles. The amount of coating applied to the softener core particles is typically from about 2% to about 30%, preferably about 3% to about 15% by weight of total particle (i.e., core plus coating).

Alternatively, other types of encapsulating processes such as described in an article by Nack entitled "Microencapsulation Techniques, Applications and Problems," J. Soc. Cos. Chem., Vol. 21, Pages 85-98 (Feb. 4, 1970), incorporated herein by reference, can be used. The processes disclosed in U.S. Pat. No. 4,234,627, supra. incorporated herein by reference, can also be used.

If it is desired to agglomerate the softener/MA particles, this can be accomplished in the following manner. The softener particles are fed to a highly efficient mixer (e.g., Schugi Flexomix Model 160,335 or 400 from Schugi Process Engineers USA, 41-T Tamarack Circle, Skillman, New Jersey 08558), or a pan agglomerator. Aqueous solution or dispersion of agglomerating agent is sprayed onto the moving particles causing them to stick to each other. The water is evaporated and the dried agglomerated particles are sized by sieving. Suitable agglomerating agents include dextrin starches, Pluronic Polyols (copolymers of ethylene oxide and/or propylene oxide with either ethylene glycol or propylene glycol) and hydratable salts such as sodium tripolyphosphate or sodium sulfate.

The type of apparatus described in U.S. Pat. No. 3,196,827 (Wurster et al.), cited suora. can also be used for agglomerating particles.

(4) Detergent Compositions

The dryer-activated softener particles containing perfume/cylodextrin complexes of the present invention can be formulated into detergent compositions. Such compositions typically comprise detersive surfactants and detergency builders and, optionally, additional ingredients such as bleaches, enzymes, fabric brighteners and the like. The particles are present in the detergent composition at a level sufficient to provide from about 0.5% to about 10%, and preferably from about 1% to about 5% of quaternary ammonium fabric softener in the detergent composition. The remainder of the detergent composition will comprise from about 1% to about 50%, preferably from about 10% to about 25% detersive surfactant, and from about 10% to about 80%, preferably from about 20% to about 50% of a detergency builder, and, if desired, other optional laundry detergent components.

(a) The Surfactant

Surfactants useful in the detergent compositions herein include well-known synthetic anionic, nonionic, amphoteric and zwitterionic surfactants. Typical of these are the alkyl benzene sulfonates, alkyl- and alkylether sulfates, paraffin sulfonates, olefin sulfonates, alkoxylated (especially ethoxylated) alcohols and alkyl phenols, amine oxides, alpha-sulfonates of fatty acids and of fatty acid esters, alkyl betaines, and the like, which are well known from the detergency art. In general, such detersive surfactants contain an alkyl group in the $C_9$–$C_{18}$ range. The anionic detersive surfactants can be used in the form of their sodium, potassium or triethanolammonium salts; the nonionics generally contain from about 5 to about 17 ethylene oxide groups. $C_{11}$–$C_{16}$ alkyl benzene sulfonates, $C_{12}$–$C_{18}$ paraffin-sulfonates and alkyl sulfates are especially preferred in the compositions of the present type.

A detailed listing of suitable surfactants for the detergent compositions herein can be found in U.S. Pat. No. 3,936,537, Baskerville, issued Feb. 3, 1976, incorporated by reference herein. Commercial sources of such surfactants can be found in McCutcheon s EMULSIFIERS AND DETERGENTS, North American Edition, 1984, McCutcheon Division, MC Publishing Company, also incorporated herein be reference.

(b) Detergency Builders

Useful detergency builders for the detergent compositions herein include any of the conventional inorganic and organic water-soluble builder salts, as well as various water-insoluble and so-called "seeded" builders.

Nonlimiting examples of suitable water-soluble, inorganic alkaline detergent builder salts include the alkali metal carbonates, borates, phosphates, polyphosphates, tripolyphosphates, bicarbonates, silicates, and sulfates. Specific examples of such salts include the sodium and potassium tetraborates, bicarbonates, carbonates, tripolyphosphates, pyrophosphates, and hexametaphosphates.

Examples of suitable organic alkaline detergency builder salts are: (1) water-soluble amino polyacetates, e.g., sodium and potassium ethylenediaminetetraacetates, nitrilotriacetates, and N-(2-hydroxyethyl)nitrilodiacetates; (2) water-soluble salts of phytic acid, e.g., sodium and potassium phytates; (3) watersoluble polyphosphonates, including sodium, potassium and lithium salts of ethane-1-hydroxy-1,1-diphosphonic acid, sodium, potassium, and lithium salts of methylenediphosphonic acid and the like.

Seeded builders include such materials as sodium carbonate or sodium silicate, seeded with calcium carbonate or barium sulfate.

Examples of suitable organic alkaline detergency builder salts are: (1) water-soluble amino polyacetates, e.g., sodium and potassium ethylenediaminetetraacetates, nitrilotriacetates, and N-(2-hydroxyethyl)nitrilodiacetates; (2) water-soluble salts of phytic acid, e.g., sodium and potassium phytates; (3) watersoluble polyphosphonates, including sodium, potassium and lithium salts of ethane-1-hydroxy-1,1.diphosphonic acid, sodium, potassium, and lithium salts of methylenediphosphonic acid and the like.

Seeded builders include such materials as sodium carbonate or sodium silicate, seeded with calcium carbonate or barium sulfate. Hydrated sodium Zeolite A having a particle size of less than about 5 microns is particularly desirable.

A detailed listing of suitable detergency builders can be found in U.S. Pat. No. 3,936,537, supra, incorporated herein by reference.

(c) Optional Detergent Ingredients

Optional detergent composition components include enzymes (e.g., proteases and amylases), halogen bleaches (e.g., sodium and potassium dichloroisocyanurates), peroxyacid bleaches (e.g., diperoxydodecane-1,12-dioic acid), inorganic percompound bleaches (e.g., sodium perborate), activators for perborate (e.g., tetraacetylethylenediamine and sodium nonanoyloxybenzene sulfonate), soil release agents (e.g., methylcellulose), soil suspending agents (e.g., sodium carboxymethylcellulose) and fabric brighteners.

(d) Pouched Compositions

When fabric softener particles of the invention are added to the wash step of a laundering process, it is inevitable that some of the particles will not adhere to or become trapped in the folds of the fabrics and will, therefore, be lost in the discarded wash solution or rinse water. In order to avoid such loss, the particles can be added to the wash solution in a sealed, porous water-insoluble pouch such as the type described in U.S. Pat. No. 4,223,029, Mahler et al., issued Sep. 16, 1980, incorporated by reference herein. Detergent granules can be included in the pouch with the softener particles. When the pouch is placed in water in the wash step of the laundering process, the detergent dissolves, but the softener particles remain in the pouch. The pouch remains with the fabrics through the wash and rinse. When the pouch is tumbled with the fabrics in the dryer, the softener particles release the softener, which melts onto the pouch material and is transferred from the pouch material to the fabrics as the pouch comes into contact with the fabrics during the drying cycle.

Preferred pouch structures are multi-pouch porous sheet structures such as described in application U.S. Ser. No. 675,804, Bedenk et al., filed Nov. 28, 1984, now U.S. Pat. Nos. 4,638,907, Bedenk/Harden, issued Jan. 27, 1987; and 4,259,383, Eggensperger et al., issued Mar. 31, 1981, both incorporated herein by reference. In a single pouch structure, the particles tend to collect in a relatively small area of the structure, whereas in a multipouch sheet structure the softener particles are distributed over a larger area of the structure thereby facilitating more even transfer of softener to fabrics in the dryer.

Suitable pouch materials include, paper, nonwoven synthetics such as spunbonded and wet laid polyester, and porous formed film plastic sheet material.

2. PERFUMES

Heretofore, most laundry products, including detergents and fabric softening products, have contained some perfume to deposit some fragrance on the laundered fabrics, both to provide an olfactory aesthetic benefit and to serve as a signal that the fabrics are clean. Due to the high energy input and large air flow in the drying process used in the typical automatic laundry dryers, a large part of the perfume provided by such laundry products has been lost out the dryer vent. Even for the less volatile components, as described hereinafter, only a small fraction remains on the fabrics after the drying cycle. The loss of the highly volatile fraction of the perfume, as described hereinafter, is much higher. Usually the loss of the highly volatile fraction is practically total. Due to this effect most laundry perfumes have been composed mainly of less volatile, high boiling (having high boiling points), perfume components to survive the drying cycle and thus provide better "fabric substantivity." The main function of a small fraction of the highly volatile, low boiling (having low boiling points), perfume components in these perfumes is to improve the fragrance odor of the product itself, rather than impacting on the subsequent fabric odor. However, some of the volatile, low boiling perfume ingredients can provide a fresh and clean impression to the fabrics, and it is highly desirable that these ingredients be deposited and present on the dried fabrics.

The perfume ingredients and compositions of this invention are the conventional ones known in the art. Selection of any perfume component, or amount of perfume, is based solely on aesthetic considerations. Suitable perfume compounds and compositions can be found in the art including U.S. Pat. Nos. 4,145,184, Brain and Cummins, issued Mar. 20, 1979; 4,209,417, Whyte, issued Jun. 24, 1980; 4,515,705, Moeddel, issued May 7, 1985; and 4,152,272, Young, issued May 1, 1979, all of said patents being incorporated herein by reference. Normally, the art recognized perfume compositions are relatively substantive as described hereinafter to maximize their odor effect on fabrics. However, it is a special advantage of perfume delivery via the perfume/cyclodextrin complexes in softeners in the dryer that nonsubstantive perfumes are effective.

A substantive perfume is one that contains a sufficient percentage of substantive perfume materials so that when the perfume is used at normal levels in laundry products, it deposits a desired odor on the laundered fabrics. In general, the degree of substantivity of a perfume is roughly proportional to the percentages of substantive perfume material used. Relatively substantive perfumes contain at least about 1%, preferably at least about 10%, substantive perfume materials.

Substantive perfume materials are those odorous compounds that deposit on fabrics via the laundry process and are detectable by people with normal olfactory acuity. Such materials typically have vapor pressures lower than that of the average perfume material. Also, they typically have molecular weights of about 200 or above, and are detectable at levels below those of the average perfume material.

Perfumes can also be classified according to their volatility, as mentioned hereinbefore. The highly volatile, low boiling, perfume ingredients typically have boiling points of about 250° C. or lower. Many of the more moderately volatile perfume ingredients are also lost substantially in the drying cycle. The moderately volatile perfume ingredients are those having boiling points of from about 250° C. to about 300° C. The less volatile, high boiling, perfume ingredients referred to hereinbefore are those having boiling points of about 300° C. or higher. A significant portion of even these high boiling perfume ingredients, considered to be fabric substantive, is lost during the drying cycle, and it is desirable to have means to retain more of these ingredients on the dried fabrics. Many of the perfume ingredients, along with their odor character, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo.-menthyl acetate, menthone, iso-menthone, myrcene, myrcenyl acetate, myrcenol, nerol, neryl acetate, nonyl acetate, phenyl ethyl alcohol, alphapinene, beta-pinene, gamma-terpinene, alpha-terpineol, beta-ter-pineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95° % of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gammamethyl ionone, nerolidol, patchouli alcohol, phenyl hexanol, betaselinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-1O-carboxaldehyde), methyl cedrylone, methyl dihydro jasmonate, methylbeta-naphthyl ketone, musk indanone, musk ketone, musk tibetene, and phenylethyl phenyl acetate.

Cyclodextrin inclusion complexes (perfume/cyclodextrin, or perfume/CD, complexes), as described hereinafter, of the high boiling, the moderately volatile, and the low boiling perfume ingredients are stable (a) throughout the mixing of the complexes with the molten fabric softener mixes, especially when the fabric softener mixes contain some clay as described hereinafter, and the coating of the resulting fabric softening compositions onto the flexible substrate to form the fabric conditioning sheets, (b) during the drying of the wet fabrics in the tumble dryer, and (c) during the wear of the dry fabrics.

3. CYCLODEXTRINS

As used herein, the term "cyclodextrin" (CD) includes any of the known cyclodextrins such as unsubstituted cyclodextrins containing from six to twelve glucose units, especially, alpha-, beta-, and gamma-cyclodextrins, and/or their derivatives, and/or mixtures thereof, that are capable of forming inclusion complexes with perfume ingredients. Alpha-, beta-, and gamma-cyclodextrins can be obtained from, among others, American Maize-Products Company (Amaizo). There are many derivatives of cyclodextrins that are known. Representative derivatives are those disclosed in U.S. Pat. Nos: 3,426,011, Parmerter et al., issued Feb. 4, 1969; 3,453,257, 3,453,258, 3,453,259, and 3,453,260, all in the names of Parmerter et al., and all issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,638,058, Brandt et al., issued Jan. 20, 1987; 4,746,734, Tsuchiyama et al., issued May 24, 1988; and 4,678,598, Ogino et al., issued Jul. 7, 1987, all of said patents being incorporated herein by reference. Examples of cyclodextrin derivatives suitable for use herein are methyl-$\beta$-CD, hydroxyethyl-$\beta$-CD, and hydroxypropyl-$\beta$-CD of different degrees of substitution (D.S.), available from Aldrich Chemical Company. Water-soluble derivatives are also highly desirable.

The individual cyclodextrins can also be linked together, e.g., using multifunctional agents to form oligomers, polymers, etc. Examples of such materials are available commercially from Amaizo and from Aldrich Chemical Company ($\beta$-CD/epichlorohydrin copolymers).

It is also desirable to use mixtures of cyclodextrins and/or precursor compounds to provide a mixture of complexes. Such mixtures can provide more even odor profiles by encapsulating a wider range of perfume ingredients and/or preventing formation of large crystals of said complexes. Mixtures of cyclodextrins can conveniently be obtained by using intermediate products from known processes for the preparation of cyclodextrins including those processes described in U.S. Pat. Nos.: 3,425,910, Armbruster et al., issued Feb. 4, 1969; 3,812,011, Okada et al., issued May 21, 1974; 4,317,881, Yagi et al., issued Mar. 2, 1982; 4,418,144, Okada et al., issued Nov. 29, 1983; and 4,738,923, Ammeraal, issued Apr. 19, 1988, all of said patents being incorporated herein by reference. The additional ingredients present in such intermediate products, including unreacted starch and/or linear and/or branched dextrin and/or denatured proteins (enzyme residues) and/or mixtures thereof, are compatible and can provide additional, less stable complexes, etc. Such less stable complexes can provide more immediate perfume release upon rewetting. Preferably at least a major portion of the cyclodextrins are beta-and/or gamma-cyclodextrins.

A. Complex Formation

The complexes of this invention are formed in any of the ways known in the art. Typically, the complexes are formed either by bringing the perfume and the cyclodextrin together in a suitable solvent, or by kneading the ingredients together in the presence of a minimal amount of solvent. The kneading method is particularly desirable because less solvent is needed and therefore less separation of the solvent is required. Suitable processes are disclosed in the patents incorporated hereinbefore by reference. Additional disclosures of complex formation can be found in Atwood, J.L., J.E.D. Davies & D.D. MacNichol, (Ed.): Inclusion Comoounds, Vol. III, Academic Press (1984), especially Chapter 11 and Atwood, J.L. and J.E.D. Davies (Ed.): Proceedinqs of the Second International Svoosium of Cvclodextrins Tokyo, Japan, (July, 1984), both of said publications being incorporated by reference.

In general, perfume/cyclodextrin complexes have a molar ratio of perfume compound to cyclodextrin of 1:1. However, the molar ratio can be either higher or lower, depending on the size of the perfume compound and the identity of the cyclodextrin compound. The molar ratio can be determined easily by forming a saturated solution of the cyclodextrin and adding the perfume to form the complex. In general the complex will precipitate readily. If not, the complex can usually be precipitated by the addition of electrolyte, change of pH, cooling, etc. The complex can then be analyzed to determine the ratio of perfume to cyclodextrin.

As stated hereinbefore, the actual complexes are determined by the size of the cavity in the cyclodextrin and the size of the perfume molecule. Although the normal complex is one molecule of perfume in one molecule of cyclodextrin, complexes can be formed between one molecule of perfume and two molecules of cyclodextrin when the perfume molecule is large and contains two portions that can fit in the cyclodextrin. Highly desirable complexes can be formed using mixtures of cyclodextrins since perfumes are normally mixtures of materials that vary widely in size. It is usually desirable that at least a majority of the material be beta- and/or gamma-cyclodextrin. It is highly desirable to use the reaction mixtures from the intermediate stages of the manufacture of the pure cyclodextrins as discussed hereinbefore. The presence of the original source materials is usually not objectionable and the presence of mixtures of cyclodextrins is usually desirable. For example, if one carries out the preparation of cyclodextrins from starch as described in U.S. Pat. No. 3,425,910, Armbruster/Kooi, issued Feb. 4, 1969, one obtains a reaction mixture containing about 40% of a mixture of cyclodextrins, consisting mainly of the beta form. The remaining portion of the reaction mixture consists mainly of noncyclic dextrins from the starch hydrolysate. Preparing the perfume/cyclodextrin inclusion complexes directly from this reaction mixture and isolating the resulting mixture by some suitable means, for example freeze-drying, produces an acceptable, and usually desirable material for the purposes of this invention.

It should be noted that the ratio of cyclodextrins to non-cyclic dextrins, and the ratio of the different forms of the cyclodextrins resulting from this type of preparation varies considerably depending on the sources of the enzymes and the starch, and other reaction conditions including time, temperature, pH, and concentration. Some of these variations are described in U.S. Pat. Nos. 3,812,011, Okada, Tsuyama, and Tsuyama, issued May 21, 1974; 4,317,881, Yagi, Kouno and Inui, issued Mar. 2, 1982; 4,418,144, Okada, Matsuzawa, Uezima, Nakakuki, and Horikoshi, issued Nov. 29, 1983; 4,378,923, Ammeraal, issued Apr. 19, 1988, all of said patents being incorporated herein by reference. Materials obtained by any of these variations are acceptable for the purposes of this invention.

It is also acceptable to isolate the inclusion complexes directed from the reaction mixture by crystallization. For example, if one carries out the preparation of the cyclodextrins as above in the presence of the perfume, the inclusion complex usually precipitates out as it is formed. This precipitate is composed mainly of a mixture of the inclusion complexes of the various cyclodextrins (alpha, beta, gamma, and higher order), although some noncyclic dextrins, as well as perfume complexes with these noncyclic dextrins can be present.

Continuous operation usually involves the use of supersaturated solutions, and/or kneading, and/or temperature manipulation, e.g., heating and then either cooling, freeze-drying, etc. The complexes may be dried or not depending on the next step in the process for making the fabric softener composition. In general, the fewest process steps are used to avoid loss of perfume.

A desirable variation involves forming a complex with only a portion of the perfume to provide both an initial odor and delayed odor. By using the perfume/cyclodextrin complexes, it is possible to provide a wide variety of unique perfume profiles in terms of timing and/or perfume composition.

The term "fabric conditioning composition" as used herein is defined as a mixture of perfume/cyclodextrin complex and fabric softening and/or antistatic agent as defined herein.

B. Complex Particle Sizes

The particle sizes of the complexes are selected according to the desired perfume release profile. Small particles, e.g., from about 0.01 $\mu$m to about 10 $\mu$m, preferably from about 0.01 $\mu$m to about 8 $\mu$m, more preferably from about 0.05 $\mu$m to about 5 $\mu$m, are desirable for providing a quick release of the perfume when the dryed fabrics are rewetted. These small particles are conveniently prepared by the kneading method. Larger particles, e.g., those having particle sizes of from about 10 $\mu$m to about 1,000 $\mu$m preferably from about 10 $\mu$m to about 250 $\mu$m, more preferably from about 10 $\mu$m to about 50 $\mu$m, are unique in that they can provide either slow release of perfume when the dryed fabrics are rewetted with a large amount of water or a series of perfume releases when the fabrics are rewetted a plurality of times. They are also desirable for application directly to damp fabrics. They release some perfume upon contact with damp fabrics, but retain sufficient perfume to provide perfume effects when the fabrics are rewetted. The larger particle size complexes are conveniently prepared by a crystallization method in which the complexes are allowed to grow, and large particles are ground to the desired sizes if necessary. Mixtures of small and large particles can give a broader perfume profile. Therefore, it is desirable to have substantial amounts of particles both below and above 10 microns.

4. VISCOSITY CONTROL AGENTS

Very useful ingredients are viscosity control agents, especially particulate clays, which are especially useful in the substrate articles. Examples of the particulate clays useful in the present invention are described in U.S. Pat. No. 4,103,047, supra, which is incorporated herein by reference. A preferred clay viscosity control agent is calcium bentonite clay, available from Southern Clay Products under the trade name Bentolite® L. The clay viscosity control agent is preferably present at a level of from about 0.5% to about 15%, more preferably from about 1.5% to about 10% by weight of the fabric conditioning composition.

The complexes can be protected during, e.g., the preparation of the substrate articles described hereinbefore by the use of the preferred clay viscosity control materials described hereinbefore. The complexes are especially vulnerable to the effect of nonionic surfactants, fatty ($C_{8-22}$) acid esters, fatty acids, fatty alcohols, etc. If the clay is not present, some of the perfume is displaced from the complex by ingredients in the softener. However, if the clay is present, the integrity of the complex is maintained. Since both the perfume/CD complex and the clay affect (increase) the viscosity and/or the yield point of the molten fabric conditioning composition, the amount of clay required for viscosity reasons is less with the presence of more complex. However, at least a certain amount of clay should be present, e.g., at least about 2%, preferably at least about 5% by weight of the complex, to provide protection of the perfume from displacement out of the complex by fabric softener and/or conditioning composition ingredients.

5. OPTIONAL INGREDIENTS

Well known optional components included in the fabric conditioning composition which are useful in the present invention are narrated in U.S. Pat. No. 4,103,047, Zaki et al., issued Jul. 25, 1978, "Fabric Treatment Compositions," incorporated herein by reference.

A. Uncomplexed (Free) Perfume

A preferred optional ingredient is free perfume, other than the perfume which is present as the perfume/cyclodextrin complex, which is also very useful for imparting odor benefits, especially in the product and/or in the dryer. Preferably, such uncomplexed perfume contains at least about 1%, more preferably at least about 10% by weight of said uncomplexed perfume, of substantive perfume materials. Such uncomplexed perfume is preferably present at a level of from about 0.10% to about 10% by weight of the portion of the composition that is transferred to the fabrics, e.g., everything but the dispensing means in substrate articles.

B. Polymeric Soil Release Agents

Especially desirable optional ingredients are polymeric soil release agents, preferably those comprising block copolymers of polyalkylene terephthalate and polyoxyethylene terephthalate, and block copolymers of polyalkylene terephthalate and polyethylene glycol. Preferably, these polymeric soil release agents contain one, or more, negatively charged functional groups such as the sulfonate functional group, preferably as capping groups at the terminal ends of said polymeric soil release agent. The soil release agent is preferably present at a level of from about 1% to about 70%, more preferably from about 10% to about 60%, and most preferably from about 15% to about 50%, by weight of the fabric conditioning composition.

The polymeric soil release agents, including nonionic, etc., agents, preferably become molten at temperatures no higher than about 90° C. and have viscosities above about 10,000 cps at 85° C. Other polymeric soil release agents with higher melting points can be used when they dissolve in a viscosity reducing agent, especially those viscosity reducing agents which can act as solvents for the polymeric soil release agent.

(1) Anionic Polymeric Soil Release Agent

The preferred polymeric soil release agents useful in the present invention include anionic polymeric soil release agents (ASRP's). Anionic polymeric soil release agents are compatible with the cationic softener agents of this invention and they are effective. Suitable anionic polymeric or oligomeric soil release agents are disclosed in U.S. Pat. No. 4,018,569, Trinh, Gosselink and Rattinger, issed Apr. 4, 1989, said patent being incorporated herein by reference.

The anionic soil release agent is preferably present at a level of from about 1% to about 70%, more preferably from about 10% to about 60%, and most preferably from about 15% to about 50%, by weight of fabric conditioning composition.

Anionic polymeric (or oligomeric) soil release agents useful in the present invention have at least one basically hydrophobic moiety; at least one hydrophilic moiety comprising one or more anionic groups; and, preferably, one or more polyoxyethylene groups.

The hydrophobic moieties comprise oligomeric, or cooligomeric, or polymeric, or copolymeric esters, amides or ethers which taken as a moiety are hydrophobic. The preferred hydrophobic moieties are oligomeric or polymeric esters which comprise alternating terephthaloyl (T) groups, and (AO) groups which are oxyalkyleneoxy, preferably oxy-1,2-alkyleneoxy groups, each alkylene group containing from 2 to about 6 carbon atoms. Other uncharged dicarbonyl groups, especially other aryldicarbonyl groups can be present, at least in a small percentage. Oxyethyleneoxy, oxy-1,2-propyleneoxy, and mixtures thereof are the most preferred (AO) groups for the hydrophobic moieties.

The hydrophilic anionic moieties contain one or more covalently bonded anionic groups such as sulfonate, sulfate, carboxylate, phosphonate, or phosphate groups where said anionic groups are paired with compatible cations. The hydrophilic moieties can optionally comprise nonionic hydrophilic groups in addition to the anionic groups. The preferred hydrophilic anionic moieties contain one or more sulfonate groups. The anionic moieties can either be at the ends of the polymer molecules, e.g., chains, (capping groups) or positioned internally along the polymer molecules, e.g., chains. Preferred anionic capping moieties are sulfoaroyl groups, especially sulfobenzoyl groups, and sulfopolyoxyethylene groups, $MO_3S(CH_2CH_2O)_n$-, where M is preferably a compatible cation, and each n is from 1 to about 30, preferably from 1 to about 15, most preferably from 1 to about 3. Internal hydrophilic anionic moieties along the chain are preferably 5-sulfoisophthaloyl groups.

A generic empirical formula for some preferred ASRP's is $(CAP)_x(AO)_y(T)_z(I)_q(En)_r$ wherein: $(AO)_y$ and $(T)_z$ are combined, at least in part, to form one or more hydrophobic moieties; at least one of $(CAP)_x$ and $(I)_q$ comprises the hydrophilic anionic moiety or moieties; and $(En)_r$ represents the poly(oxyethylene) group or groups.

In the above generic empirical formula, the following definitions apply:

(1) Each (CAP) represents an end-capping moiety selected from (a) sulfoaroyl groups; (b) groups having the formula

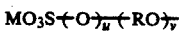

wherein each M is a compatible cation; u is 0 or 1, preferably 0; R is either an ethylene group or mixtures of ethylene and 1,2-propylene groups, and v is from 1 to about 100, preferably from 1 to about 30, more preferably from 1 to about 15; (c) poly(oxyethylene) monoalkyl ether groups, $XO-(CH_2CH_2O)_w-$, wherein X is an alkyl group containing from 1 to about 6 carbon atoms, preferably 1 carbon atom and w is from 1 to about 100, preferably from about 6 to about 25; and (d) mixtures thereof. The end-capping moieties are preferably (a), (b), or mixtures thereof, most preferably (a) and x is from 0 to 2, preferably 1 or 2, most preferably about 2.

(II) Each (AO) represents an oxyalkyleneoxy group, excluding oxyalkyleneoxy groups of (I) and (V), containing from 2 to about 6 carbon atoms, preferably 1,2-oxyalkyleneoxy, and most preferably oxyethyleneoxy, oxy-1,2-propyleneoxy, or mixtures thereof, and y is from about 1 to about 80, preferably from about 1 to about 10, most preferably from about 1.25 to about 8.

(111) Each (T) represents a terephthaloyl group. Other noncharged dicarbonyl groups can be present, at least in a small percentage, and especially other noncharged aryl dicarbonyl groups, and z is from about 1 to about 50, preferably, from about 1 to about 10, most preferably from about 1.25 to about 8.

(IV) Each (I) represents an internal anionic group, preferably selected from the group consisting of sulfoaryldicarbonyl groups, sulfoalkylenedicarbonyl groups, and mixtures thereof. The more preferred (1) is selected from the group consisting of sulfobenzene-1,2-dicarbonyl groups; sulfobenzene-1,3-dicarbonyl groups; sulfobenzene-1,4-dicarbonyl groups; and mixtures thereof. The most preferred (1) is a 5-sulfoisophthaloyl group, and q is from 0 to about 30, preferably from 0 to about 5.

(V) Each (En) represents a poly(oxyethylene)oxy group $-(OCH_2CH_2)_nO-$ wherein each n is from 2 to about 200, preferably from about 6 to about 100, most preferably from about 10 to about 80, and r is from about 0.5 to about 25, preferably from about 0.5 to about 5, most preferably from about 1 to about 2.

(VI) (CAP) and (I) are selected such that said ARSP s contain at least one anionic group.

The ASRP's can have molecular weights of from about 500 to about 40,000, preferably from about 1,000 to about 10,000. ASRP's have a balance at hydrophobicity and hydrophilicity that permits them to effectively deposit on fabric surfaces.

Compatible cations include alkali metal (especially sodium and/or potassium), and substituted ammonium (e.g., mono-, di-, or triethanolammonium or tetramethylammonium) cations. Sodium is highly preferred.

Polymers without substantial poly(oxyethylene) content are higher melting (M.P. above about 110° C.) and therefore are more difficult to formulate.

Desirable lower melting (M.P. of less than about 90 C) polymers have poly(oxyethylene) groups containing from about 20 to about 100 oxyethylene units. These high viscosity ASRP s can be blended with the fabric conditioning agents by melting and blending with the viscosity reducing agents. "Melting points" (M.P.) are determined by either any conventional melting point determination apparatus, or by observing the phase transition in a differential scanning calorimetry apparatus.

Specific ASRP's of interest include those of the U.S. Pat. application of Rene Maldonado, Toan Trinh and Eugene Paul Gosselink for SULFOAROYL END-CAPPED ESTER OLIGOMERS SUITABLE AS SOIL RELEASE AGENTS IN DETERGENT COMPOSITIONS AND FABRIC-CONDITIONER ARTICLES, Ser. No. 105,421, filed Sept. 4, 1987, said application being incorporated herein by reference.

Molecular Geometry—The preferred esters are preferably "substantially linear", in the sense that they are not significantly branched or crosslinked by virtue of the incorporation into their structure of units having more than two ester-bond forming sites. (For a typical example of polyester branching or crosslinking, see U.S. Pat. No. 4,554,328, Sinker et al., issued Nov. 19, 1985, and incorporated herein by reference.) Furthermore, no cyclic esters are essential, but can be present in the compositions at low levels as a result of side-reactions during ester synthesis. Preferably, cyclic esters will not exceed about 2% by weight of the compositions; most preferably, they will be entirely absent from the compositions.

Contrasting with the above, the term "substantially linear" as applied to the esters herein does, however, expressly encompass materials which contain side-chains which are unreactive in ester-forming or transesterification reactions. Thus, oxy-1,2-propyleneoxy units are of an unsymmetrically substituted type essential in the preferred embodiment; their methyl groups do not constitute what is conventionally regarded as "branching" in polymer technology (see Odian, Principles of Polymerization, Wiley, N.Y., 1981, pages 18-19, with which the present definitions are fully consistent), are unreactive in ester-forming reactions, and are highly desirable for the purposes of the invention. Optional units in the esters of the invention can likewise have side-chains, provided that they conform with the same nonreactivity criterion.

A specific soil release agent of the type disclosed in U.S. Ser. No. 105,421, supra. and useful in the present invention is:

Soil Release Agent I

An ester composition is made from m-sulfobenzoic acid monosodium salt, poly(ethylene glycol) (M.W. =3400), 1,2-propylene glycol and dimethyl terephthalate. Soil Release Agent I illustrates an ester composition wherein the doubly-capped ester molecules not only have sulfonated end-capping units by way of hydrophilic units, but also incorporate uncharged, i.e., nonionic, hydrophilic units in the ester backbone. Also illustrated is a catalyst addition sequence differing from that of the previous soil release agents.

Into a 250 ml, three-necked, round bottom flask, fitted with a thermometer, magnetic stirrer and modified Claisen head, the latter connected to a condenser and receiver flask, are placed, under argon, m-sulfobenzoic acid monosodium salt (13.2 g; 0.059 moles; Eastman Kodak) and 1,2-propylene glycol (35.7 g, 0.47 moles, Fisher). The mixture is stirred and heated steadily under argon at atmospheric pressure, to reach a temperature of about 200° C. The reaction conditions are kept constant, while distillate (1.06 g; 100% based on the theoretical yield of wate collecting in the receiver flask, and the temperature is then allowed to fall to about 170°-175° C. To the clear, colorless reaction mixture are added, under argon, hydrated monobutyltin(IV) oxide (0.2 g; 0.1% w/w), dimethyl terephthalate (45.0 g; 0.23 moles.. Aldrich), and HO(CH2CH2O)nH (1OO.O g; 0.029 moles; n averages 77; M.W. =3400; Aldrich). Also added, as antioxidant, is BHT (0.2 g; Aldrich). Over 18-19 hours, the mixture is stirred and heated under argon at atmospheric pressure, at temperatures ranging from about 175°-195° C.; this reaction period is followed by a further 4 hour reaction period in which all reaction conditions, with the exception of temperature (now raised to about 200° C.), are unchanged. The methanol which is liberated in the transesterification is continuously collected. The mixture is cooled to about 50° C. and is transferred under argon to a Kugelrohr apparatus (Aldrich). The apparatus is evacuated to a pressure of 0.1 mm Hg. While maintaining the vacuum and stirring, the temperature is raised to 200° C., and the temperature is then held constant for about 10 hours to allow completion of the synthesis. (In an alternative procedure, n.m.r. spectroscopic monitoring confirms that the reaction is substantially complete after only 6-8 hours.) During this period, excess glycols distill from the homogeneous mixture.

In referring to the ester composition of this example, the following conventions will be used:

| | |
|---|---|
| (CAP) = end-capping units | (i) |
| (PG) = oxy-1,2-propyleneoxy units | (ii) |
| (T) = terephthaloyl units | (iii) |
| ($E_n$) = poly(oxyethylene)oxy units, average degree of ethoxylation = n | (iv) |

Using the above convention, Soil Release Agent I has the empirical formula representation:

$(CAP_2(PG)_8(T)_8(E_{77})_1$.

A product made according to the above procedure had a transition point range of from about 40° C. to about 5° C. as determined by a differential scanning calorimetry method, and had a viscosity of from about 15,000 to about 40,000 cps at 85° C. and 3.84 sec$^{-1}$ shear rate.

Other suitable ASRP s are those described in U.S. Pat. No. 4,721,580 of Eugene P. Gosselink for ANIONIC END-CAPPED OLIGOMERIC ESTERS AS SOIL RELEASE AGENTS IN DETERGENT COMPOSITIONS, issued Jan. 26, 1988, said patent being incorporated herein by reference.

Alternative, effective anionic soil release esters useful in the present invention have anionic capping groups Q, Q' and Q" which are the same or different and are selected from groups

wherein M is H or a salt-forming cation, L is phenoxyethoxy, phenoxypropoxy or $C_1$-$C_6$ alkoxy, Y is —$CH_2CH(CH_3)$— or —$CH(CH_3)CH_2$—, q is 1 or 0, m is an integer from 0 to 15 provided that m+q is at least 1, and r is an integer from 0 to 30. Mixtures of these alternatively capped esters with the hereinbefore defined

capped esters are likewise effective soil release agents.

(2) Nonionic Polymeric Soil Release Agent

A preferred polymeric soil release agent is a crystallizable polyester copolymer with repeat units of ethylene terephthalate units containing 10-50% by weight of polyoxyethylene terephthalate units together with 90-50% by weight of polyoxyethylene terephthalate units, derived from a polyoxyethylene glycol of average molecular weight of from about 300 to about 6,000, and the molar ratio of ethylene terephthalate units to polyoxyethylene terephthalate units in the crystallizable polymeric compound is between 2:1 and 6:1. A more preferred polymer is that wherein the polyoxyethylene terephthalate units are derived from a polyoxyethylene glycol with an average molecular weight of from about 1,000 to about 4,000. These polymers are disclosed in U.S. Pat. No. 3,416,952, McIntyre and Robertson, issued Dec. 17, 1968, incorporated herein by reference. Examples of these copolymers include the commercially available material Zelcon ® 4780 (from DuPont) and Milease ® T (from ICI), both have the Chemical Abstracts Service Registry No. 9016-88-0. Both Zelcon 4780 and Milease T are sold in the aqueous dispersion form containing up to 85% water. It is preferable to use the dehydrated polymer to prepare the fabric conditioning composition in order to avoid the incorporation of excess moisture which is believed to make the resulting fabric conditioning articles wet and sticky. The dehydrated polymer is obtained by drying the above-mentioned commercial dispersions, or can be obtained directly in the concentrated form from the manufacturers. An example of the latter is Zelcon PG, the concentrated form of Zelcon 4780, and is obtained from DuPont Co.

The most preferred polymer is a solid at room temperature, has a softening phase transition temperature at or above about 30.C and becomes a flowable liquid below about 100° C., preferably below about 90° C. The softening phase transition temperature can be determined by the differential scannin calorimetry method. A polymer that is a hard solid at room temperature is desirable in order to keep the fabric conditioning sheets from having a tacky feel, while its softening and fluidity at higher temperatures facilitate the substrate coating process and the subsequent fabric conditioning active transfer from the fabric conditioning sheet to the fabrics in the clothes dryer.

An example of such soil release polymer is Milease TL obtained from ICI. Milease TL is a low molecular weight nonionic block cooligomer of poly(ethylene terephthalate) and polyoxyethylene terephthalate, containing oxyethyleneoxy, terephthaloyl and poly(oxyethylene)oxy groups, said poly(oxyethylene)oxy groups containing about 34 oxyethylene units on the average. $^{13}$C nmr and viscosity data show that the Milease TL sample used in the preparation of Examples disclosed herein contains on the average about 3 oxyethyleneoxy groups, about 4 terephthaloyl groups, and about 2 poly(oxyethylene)oxy groups, with an average molecular weight of about 3700.

Other suitable polymers are disclosed in U.S. Pat. Nos.: 4,711,730, Gosselink and Diehl, issued Dec. 8, 1987; 4,808,086, Evans, Huntington, Stewart, Wolf, and Zimmerer, issued Feb. 24, 1989; and 4,702,857 Gosselink, issued Oct. 27, 1987, all of said patents being incorporated herein by reference.

6. COMPOSITIONAL ADVANTAGES OF DRYER-ACTIVATED FABRIC CONDITIONERS

Perfume delivery via the solid, dryer-activated fabric conditioning compositions of the invention in laundry fabric dryers is desirable in two ways. Product malodors can be covered by the addition of free perfume to the softener composition, and perfume can be transferred onto fabric with the softener actives in the laundry fabric dryer. Present technologies add perfume directly into the softener actives independent of the other softener components, or add the perfume in encapsulated form into the softener matrix. Encapsulated perfume can deposit on fabric and be retained for relatively long periods of time. However, most capsules that will survive processing are difficult to rupture, thus they may never release the perfume in a desirable way.

Addition of free perfume into the softener matrix allows the perfume to freely migrate creating an unstable condition and free perfume deposited on fabric dissipates fairly quickly when the fabrics are stored. If one wishes to have the perfume on fabric to last longer in storage or during wearing, it usually requires deposition of more perfume onto fabric in the laundry process. However, this often requires the product to have an undesirably high product odor and/or initial fabric odor.

The ability to have a product with low product perfume odor and an acceptable initial fabric perfume odor, but also have a long-lasting fabric perfume odor has been the goal of many development projects for consumer laundry products. The products of this invention preferably only contain enough free perfume to deliver both an acceptably low product perfume odor and an acceptable initial fabric perfume odor. Perfume incorporated into the product in the form of perfume/CD complex as part of a substrate article or in the form of solid fabric softener particles containing perfume/CD complex (in the case of detergent compatible products), will be released when the fabric is used in situations where renewed perfume odor is really and appropriately needed, e.g., when some moisture is present, such as when using wash cloths and towels in a bathroom, or when there is perspiration odor on clothes during and after a high level of physical activity.

The laundry products of this invention can also contain only the perfume/CD complex, without any noticeable amount of free perfume. In this case, the products function initially almost as unscented products. Fabrics treated with these products do not carry any obvious perfume odor that can "clash" with other expensive personal fragrances that the consumer may wish to wear. Only when extra perfume is needed, such as for bathroom use, or for perspiration, is the perfume in the complex released.

During storage of the treated fabric, a small amount of perfume can escape from the complex as a result of the equilibrium between the perfume/CD complex and free perfume and CD, and a light scent is obtained. If the product contains both free and complexed perfume, this escaped perfume from the complex contributes to the overall fabric perfume odor intensity, giving rise to a longer lasting fabric perfume odor impression.

Thus, by adjusting the levels of free perfume and perfume/CD complex it is possible to provide a wide range of unique perfume IO profiles in terms of timing and/or perfume identity. Solid, dryer-activated fabric conditioning compositions are a uniquely desirable way to apply the complexes, since they are applied at the very end of the fabric treatment regimen when the fabric is clean and when there are almost no additional treatments that can affect the perfume.

The perfume/cyclodextrin complexes are usually incorporated into the fabric conditioning compositions, especially when the compositions are to be added to laundry detergents. It is believed that when the perfume/cyclodextrin complexes are encapsulated in fabric softener, they are attached to the fabric in the laundry dryer.

Therefore, the invention also encompasses a method for imparting long-lasting perfume benefits plus softening and/or antistatic effects to fabrics in an automatic laundry dryer comprising tumbling said fabrics under heat in said dryer with an effective, i.e., softening, amount of a composition comprising softening active(s) and an effective amount of perfume/CD complex.

This invention also contributes to the aesthetics of the clothes washing process. One important point in the laundry process where the consumer appreciates the odor (fragrance) is during the wash process (i.e., from the wash water and during the transfer of wet clothes to the dryer). This aesthetic benefit is currently provided mainly by the perfume added via the detergent composition or liquid softener composition to the wash and/or rinse water. Clothes that have been pretreated, e.g., in the dryer with the methods of this invention give off a burst of fragrance in the wash water, and the resulting fabrics are "perfumy" even though no other perfume is used in the washing, rinsing and/or drying steps.

All percentages, ratios, and parts herein are by weight unless otherwise stated.

The following are nonlimiting examples of the instant articles and methods.

Four different perfumes used in the following Examples are as follows:

| Substantive Perfume (A) | | Relatively Nonsubstantive Perfume (B) | |
|---|---|---|---|
| Component | Wt. % | Component | Wt. % |
| Benzyl Acetate | 5.0 | Alpha Pinene | 5.0 |
| Benzyl Salicylate | 10.0 | Cedarwood Terpenes | 20.0 |
| Coumarin | 5.0 | Dihydro Myrcenol | 10.0 |
| Ethyl Maltol | 5.0 | Eugenol | 5.0 |
| Ethylene Brassylate | 10.0 | Lavandin | 15.0 |
| Galaxolide ® (50%) | 15.0 | Lemon Oil CP | 10.0 |
| Hexyl Cinnamic Aldehyde | 20.0 | Orange Terpenes | 15.0 |
| | | Phenyl Ethyl Alcohol | 20.0 |
| Gamma Methyl Ionone | 10.0 | Total | 100.0 |
| Lilial ® | 15.0 | | |
| Patchouli | 5.0 | | |
| Total | 100.0 | | |

Complete Perfume (C)

Perfume C is a substantive perfume which is composed mainly of moderate and nonvolatile perfume ingredients. The major ingredients of Perfume C are benzyl salicylate, para-tertiary-butyl cyclohexyl acetate, para-tertiary-butyl-alpha-methyl hydro-cinnamic aldehyde, citronellol, coumarin, galaxolide, heliotropine, hexyl cinnamic aldehyde, 4-(4-hydroxy-4-methyl pentyl)-3-cyclhexene-10-carboxaldehyde, methyl cedrylone, gamma-methyl ionone, and patchouli alcohol.

Perfume (D) (More Volatile Portion of Perfume C)

Perfume D is a rather nonsubstantive perfume which is composed mainly of highly and moderately volatile fractions of Perfume C. The major ingredients of Perfume D are linalool, alpha terpineol, citronellol, linalyl acetate, geraniol, hydroxycitronellal, terpinyl acetate, eugenol, and flor acetate.

The above-defined perfumes and others, as defined hereinafter, are used to form the following complexes, which are used in the Examples herein.

Complex 1—Citral/$\beta$-Cyclodextrin

A mixture of about 48.5 g (42.7 mmole) of $\beta$-cyclodextrin ($\beta$-CD) and 1000 ml of water is stirred vigorously and heated to 75° C., which results in a clear solution. At this temperature, about 6.5 g (42.7 mmole) of citral is added in one portion, which causes the solution to become cloudy. Within a few minutes, crystals begin to form. The reaction mixture is stirred at 75° C. for 1 hour to allow crystallization to proceed. After this period of time, the reaction mixture is filtered while hot, and the crystals are transferred to a round bottom flask and dried in vacuo. When dry, the crystals are washed thoroughly with diethyl ether, filtered, and the last traces of ether are removed in vacuo. This affords about 21.6 g (39%) of the crystalline citral/$\beta$-CD inclusion complex which is odorless when dry but produces the fragrance of citral when added to water.

Complex 2—Perfume C/$\beta$-CD

A mixture of about 16.0 g of $\beta$-CD and 300 ml of water is stirred vigorously and heated to 75° C., which results in a clear solution. At this temperature, about 2.82 g of perfume C is added in one portion, which caused the solution to become cloudy. Within a few minutes, tiny crystals begin to precipitate out. The reaction mixture is stirred at 75° C. for 1 hour to allow crystallization to proceed. After this period of time, the reaction mixture is allowed to cool to room temperature and filtered. The precipitate is transferred to a round bottom flask and dried in vacuo. When dry, the fine powder is washed thoroughly with diethyl ether, filtered, and the last traces of ether are removed in vacuo. This procedure yields about 11 g of the perfume/$\beta$-CD inclusion complex as a white powder and is odorless when dry but produces the fragrance of Perfume C when added to water. Complex 3–Perfume C/$\beta$-CD A mobile slurry is prepared by mixing about 1 kg of $\beta$-CD and 1,000 ml of water in a stainless steel mixing bowl of a KitchenAid mixer using a plastic coated heavy-duty mixing blade. Mixing is continued while about 176 g of Perfume C is slowly added. The liquid-like slurry immediately starts to thicken and becomes a creamy paste. Stirring is continued for 25 minutes. The paste is now dough-like in appearance. About 500 ml of water is added to the paste and blended well. Stirring is then resumed for an additional 25 minutes. During this time the complex again thickens, although not to the same degree as before the additional water is added. The resulting creamy complex is spread in a thin layer on a tray and allowed to air dry. This produces about 1100 g of granular solid which is ground to a fine power. The complex retains some free perfume and still has a residual perfume odor.

Complex 4

The last traces of water in Complex 3 are removed by freeze drying, after which Complex 3 loses about 1% of its weight. The resulting solid is washed with diethyl ether to remove the residual uncomplexed perfume. The last traces of ether are removed in vacuo to give Complex 4 as a white powder which is odorless when dry but produces the fragrance of Perfume C when added to water.

Complex 5

Perfume D/$\beta$-CD complex as prepared by the process of Complex 2.

Complex 6

Perfume D/$\beta$-CD complex as prepared by the process of Complex 3.

Complex 7

Perfume A/$\beta$-CD complex as prepared by the process of Complex 3.

Complex 8

Perfume B/$\beta$-CD complex as prepared by the process of Complex 3.

Complex 9—Perfume C/Methyl-$\beta$-CD (Avg. DS=1.8)

A mobile slurry is prepared by mixing about 75 g of methyl-$\beta$-CD (Average Degree of Substitution=1.8) and 100 ml of water in a beaker at room temperature using a heavy-duty overhead mechani. cal stirrer. Perfume C (15.11 g) is added to the stirred slurry in one portion and the mixture is stirred for 10 minutes. In this case, the mixture becomes slightly more mobile after the addition of the perfume. The mobile slurry is transferred to a round bottom flask, frozen in Dry Ice, and placed on a freeze dryer for lyophilization. After most of the water is removed, the resulting solid residue is ground into a powder, and washed several times with hexane. The final traces of hexane are removed in vacuo affording about 83 g of the inclusion complex as a granular solid which has a slight odor of Perfume C when dry, but produces the full fragrance of Perfume C when added to water.

Complex 10—Perfume C/Hydroxyethyl-$\beta$-CD (Avg. DS=1.6)

A mobile slurry is prepared by mixing about 99 g of hydroxyethyl-$\beta$-CD (Average Degree of Substitution=1.6) and 100 ml of water in a beaker at room temperature using a heavy-duty overhead mechanical stirrer Perfume C (12.15 g) is added to the stirred slurry in one portion and the mixture is stirred for 10 minutes. The mobile slurry is transferred to a round bottom flask, frozen in Dry Ice, and placed on a freeze dryer for lyophilization. After most of the water is removed, the resulting solid residue is ground into a powder, and washed several times with hexane. The final traces of hexane are removed in vacuo affording about 76 g of the inclusion complex as a granular solid which has a slight odor of Perfume C when dry, but produces the full fragrance of Perfume C when added to water.

Complex 11—Perfume C/Hydroxyethyl-$\beta$-CD (Avg. DS=1.0)

The above procedure is repeated using about 99 g of hydroxyethyl-$\beta$-CD (Average Degree of Substitution 1.0), 100 ml of water, and about 13.75 g of Perfume C. This affords about 110.6 g of the inclusion complex as a granular solid which has a slight odor of Perfume C when dry, but produces the full fragrance of Perfume C when added to water.

Complex 12—Perfume C/Hydroxypropyl-$\beta$-CD (Avg. DS=0.6)

The above procedure is repeated using about 99 g of hydroxypropyl-$\beta$-CD (Average Degree of Substitution=0.6), 100 ml water, and about 14.34 g of Perfume C. This affords about 111.4 g of the inclusion complex as a granular solid which has a slight odor of Perfume C when dry, but produces the full fragrance of Perfume C when added to water.

Complex 13

Perfume A is complexed with gamma-CD by the process of Complex 3.

Complex 14

Perfume C is complexed with gamma-CD by the process of Complex 3.

Complex 15—Perfume C/Cyclodextrin/Starch Mixture

Purified corn starch is liquefied at 85–90° C. by means of a liquefying enzyme (i.e., alpha amylase) until a dextrose equivalent of about 5–10 is reached. Typically, a 35% aqueous suspension of starch is used. At this point, the reaction mixture is cooled to room temperature and the cyclodextrin glucosyl transferase enzyme isolated from Bacillus macerans (according to the procedure of Tilden, Adams, and Hudson, *J. Amer. Chem. Soc.* 1942, 64, 1432) is added in the amount of about 2 activity units per gram of the starch hydrolysate. The reaction mixture is stirred at room temperature for several hours while monitoring the formation of cyclodextrins by HPLC. When the rate of cyclodextrin formation has leveled off, the reaction mixture is heated to boiling for about 1 hour to deactivate any remaining enzymes. The reaction mixture is cooled to about 60° C. and about 12% (by weight) of Perfume C based on the initial amount of starch is added. After stirring for about 1 hour at this temperature, the reaction mixture is allowed to cool to room temperature. The content of the flask is then frozen in Dry Ice and the water is removed by freeze drying (lyophilization). This affords an amber powder which contains a mixture of inclusion complexes of the various perfume components in cyclodextrins (alpha, beta, gamma, and higher order) and also complexes of the perfume components with the remaining starch fragments. This powder has some of the fragrance of Perfume C but produces more fragrance when it is added to water.

Complex 16—Perfume D/Cyclodextrin Mixture

Purified corn starch is liquified at 85°–90°O C. by means of a liquefying enzyme (i.e., alpha amylase) until a dextrose equivalent of about 5–10 is reached. At this point, the reaction mixture is cooled to room temperature and the cyclodextrin glucosyl transferase enzyme isolated from Bacillus macerans is added in the amount of about 2 activity units per gram of the starch hydrolysate along with about 12% (by weight) of Perfume D based on the initial amount of starch. This mixture is stirred at room temperature while the inclusion complex precipitates out as it is being formed. After precipitation is judged to be complete, the inclusion complex is collected, washed with ethyl acetate, and dried in vacuo affording a powder which is odorless when dry, but produces the fragrance of Perfume D when it is added to water. This powder is composed mainly of a mixture of inclusion complexes of the various perfume components in the different cyclodextrins (alpha, beta, gamma, and higher order).

Complex 17

About 300 g of $\beta$-cyclodextrin is placed in a 4-liter cylindrical stainless steel container which has baffles on the inside wall. The container is affixed to a rotating shaft and rotated continuously while about 45 g of Perfume C is sprayed slowly onto the cyclodextrin. The mixture is rotated further for about 10 minutes for a thorough impregnation of the perfume into the cyclodextrin.

The relatively nonsubstantive perfumes B and D are surprisingly effective when incorporated in the fabric conditioning compositions and products described hereinafter.

EXAMPLES OF FABRIC CONDITIONING SUBSTRATE ARTICLES

The following compositions are used in Examples 1 and 2:

| Components | Example 1 | Example 2 |
|---|---|---|
| Ditallowdimethylammonium chloride (DTDMAC) | 90.00 | 71.00 |
| Calcium bentonite clay | 5.00 | 4.00 |
| Complex 1 | 5.00 | — |
| Complex 2 | — | 25.00 |
| Totals | 100.00 | 100.00 |

Example 1

Preparation of the Coating Mix

An approximately 200 gram batch of the coating mix is prepared as follows. An amount of about 180 g of ditallowdimethylammonium chloride (DTDMAC) is melted at 80° C. The calcium bentonite clay (about 10 g of Bentolite L, available from Southern Clay Co.) is slowly added to the mixture with high shear mixing. During the mixing, the mixture is kept molten in a boiling water bath. The Complex 1 (about 10 g, washed citral/$\beta$-CD complex) is then slowly added to the mixture with high shear mixing, and the formula is mixed until the mixture is smooth and homogenous.

Preparation of Fabric Conditioning Sheets

The coating mixture is applied to preweighed nonwoven substrate sheets of about 9 inch ×11 inch (approximately 23 cm ×28 cm) dimensions. The substrate sheets are comprised of 70% 3-denier, 1-9/16 inch (approximately 4 cm) long rayon fibers with 30% polyvinyl acetate binder. The substrate weight is about 16 g per square yard (about 1.22 g/sheet). A small amount of formula is placed on a heated metal plate with a spatula and then is spread evenly with a wire metal rod. A nonwoven sheet is placed on the metal plate to absorb the coating mixture. The sheet is then removed from the heated metal plate and allowed to cool to room temperature so that the coating mix can solidify. The sheet is weighed to determine the amount of coating mixture on the sheet. The target coating is 2.0 g per sheet. If the weight is in excess of the target weight, the sheet is placed back on the heated metal plate to remelt the coating mixture and remove some of the excess. f the weight is under the target weight, the sheet is also placed on the heated metal plate and more coating mixture is added.

EXAMPLE 2

The coating mix preparation and the making of the fabric conditioning sheets are similar to those in Example 1, except that Complex 2, containing Perfume C, is used instead of Complex 1.

Fabric Treatment

A laundry load is washed in a washer with the unscented TIDE ® detergent. The wet laundry load is transferred and dried in an electric tumble dryer with a fabric conditioning sheet of Example 1 or Example 2 above. The resulting dry fabric has only very low perfume odor, but when the fabric is re-wetted a noticeably stronger perfume odor is obtained.

| Components | Example 3 | Example 4 | Example 5 |
|---|---|---|---|
| Octadecyldimethylamine | 11.89 | 11.45 | 12.37 |
| $C_{12-14}$ fatty acid | 8.29 | 7.98 | 8.62 |
| $C_{16-18}$ fatty acid | 10.69 | 10.30 | 11.12 |
| DTDMAMS | 19.32 | 18.60 | 20.10 |
| Sorbitan monostearate | 19.32 | 18.60 | 20.10 |
| Clay | 3.86 | 7.44 | — |
| Complex 2 | 26.62 | 25.63 | 27.69 |
| Totals | 100.00 | 100.00 | 100.00 |
| Coating Wt. per Sheet (g) | 2.33 | 2.42 | 2.24 |

EXAMPLE 3

A first blend of about: 11.89 parts octadecyldimethylamine (Ethyl Corporation); 8.29 parts $C_{12-14}$ fatty acid (The Procter & Gamble Co.); and 10.69 parts $C_{16-18}$ fatty acid (Emery Industries, Inc.) are melted together at 80° C., and a second blend of about 19.32 parts sorbitan monostearate (Mazer Chemicals, Inc.) and 19.32 parts ditallowdimethylammonium methylsulfate, DTDMAMS, (Sherex Chemical Co.) are melted together to form the softener component of the composition, during which time the mixture is kept molten in a boiling water bath. The calcium bentonite clay (3.86 parts Bentolite L, available from Southern Clay Co.) is then slowly added to the mixture while high shear mixing. An amount of about 26.62 parts of Complex 2 (washed inclusion complex of Perfume C in $\beta$-cyclodextrin) is then added in small portions and the formula is mixed until the mixture is smooth and completely homogenous.

The coating mixture is applied to preweighed nonwoven substrate sheets as in Example 1. The target coating is 2.33 g per sheet. Each sheet contains about 1.62 g of softener, about 0.09 g of clay, and about 0.62 g of Complex 2.

EXAMPLE 4

The coating mixture of Example 4 is prepared similarly to that of Example 3. This mixture contains relatively more clay than that of Example 3. The target coating is 2.42 g per sheet. Each sheet contains about 1.62 g of softener, about 0.18 g of clay, and about 0.62 g of Complex 2.

EXAMPLE 5

The coating mixture of Example 5 is prepared similarly to that of Example 3, but no clay is added. The target coating is 2.24 g per sheet. Each sheet contains about 1.62 g of softener, about 0.62 g of Complex 2, and no clay.

Fabric Treatment

Three laundry loads with similar garment composition are washed in washers with unscented TIDE detergent. The wet laundry loads are transferred to, and dried in, electric tumble dryers, respectively with fabric conditioning sheets of Examples 3, 4 and 5. The resulting dry fabric treated with a sheet of Example 5 (containing no clay) has a higher perfume odor than those treated with sheets of Examples 3 and 4, indicating that clay somehow helps in stabilizing perfume/CD complexes against release of the included perfume before rewetting occurs.

| Components | Example 6 | Example 7 | Example 8 |
|---|---|---|---|
| Octadecyldimethylamine | 11.89 | 10.35 | 13.06 |
| $C_{12-14}$ fatty acid | 8.29 | — | — |
| $C_{16-18}$ fatty acid | 10.69 | 18.29 | 23.07 |
| DTDMAMS | 19.32 | 17.94 | 22.63 |
| Sorbitan monostearate | 19.32 | 17.94 | 22.63 |
| Clay | 3.86 | 3.58 | 5.50 |
| Complex 3 | — | 30.89 | 10.00 |
| Complex 4 | 26.62 | — | — |
| Free Perfume C | — | 1.01 | 3.10 |
| Totals | 100.00 | 100.00 | 100.00 |
| Coating Wt. per Sheet (g) | 2.33 | 3.07 | 2.00 |

EXAMPLE 6

The coating mixture of Example 6 is prepared similarly to that of Example 3. This mixture contains Complex 4 which is made by the kneading method instead of Complex 2 which is made by the recrystallization method as in Example 3. The target coating is 2.33 g per sheet. Each sheet contains about 1.62 g of softener, about 0.09 g of clay, and about 0.62 g of Complex 4.

EXAMPLE 7

A two-component blend of about 10.35 parts octadecyldimethylamine (Ethyl Corporation) and about 18.29 parts $C_{16-18}$ fatty acid (Emery Industries, Inc.) are melted together at 80° C., and a second two-component blend of about 17.94 parts sorbitan monostearate (Mazer Chemicals, Inc.) and about 17.94 parts DTDMAMS (Sherex Chemical Co.) are melted together at 80° C. The two blends are then high-shear mixed together to form the softener component of the composition, during which time the mixture is kept molten in a boiling water bath. The calcium bentonite clay (3.58 parts Bentolite L, available from Southern Clay Co.) is then slowly added to the mixture while high shear mixing. An amount of about 30.89 parts of Complex 3 (unwashed inclusion complex of Perfume C in $\beta$-CD made by the kneading method) is then added in small portions and finally about 1.01 parts of free Perfume C is added, and the formula is mixed until the mixture is smooth and completely homogenous.

The coating mixture is applied to nonwoven substrate sheets as in Example 1. The target coating is 3.07 g per sheet. Each sheet contains about 1.98 g of softener, about 0.11 g of clay, about 0.95 g of Complex 3, and about 0.031 g of free Perfume C.

The coating mix of Example 7 contains Perfume C both in the free state to provide the initial perfume odor to the dry fabrics, and Perfume C complexed with the $\beta$-CD, to provide more Perfume C subsequently when the fabrics are re-wetted.

EXAMPLE 8

The coating mixture of Example 8 is prepared similarly to that of Example 7. This mixture contains relatively more free Perfume C than that of Example 3. The target coating is 2.0 g per sheet. Each sheet contains about 1.63 g of softener, about 0.11 g of clay, about 0.20 g of Complex 3, and about 0.062 g of free Perfume C.

| Components | Example 9 | Example 10 |
|---|---|---|
| Octadecyldimethylamine | 10.88 | 11.63 |
| $C_{12-14}$ fatty acid | 7.58 | — |
| $C_{16-18}$ fatty acid | 9.78 | 20.59 |
| DTDMAMS | 17.67 | 20.20 |
| Sorbitan monostearate | 17.67 | 20.20 |
| Clay | 3.54 | 5.99 |
| Complex 5 | 30.44 | — |
| Complex 6 | — | 18.93 |
| Free Perfume C | 2.44 | 2.46 |
| Totals | 100.00 | 100.00 |
| Coating Wt. per Sheet (g) | 2.55 | 2.52 |

EXAMPLE 9

The softener mixture of Example is prepared similarly to that of Example 3. The perfume addition is similar to that of Example 7. However, the coating mixture of Example 9 contains both Perfume C in the free state and Perfume D complexed with the $\beta$-CD (Complex 5). The free Perfume C provides the initial perfume odor to the dry fabrics, while the complexed Perfume D is used to provide the freshness impression to the re-wetted fabrics. The target coating is 2.55 g per sheet. Each sheet contains about 1.62 g of softener, about 0.09 g of clay, about 0.78 g of Complex 5, and about 0.062 g of free Perfume C.

EXAMPLE 10

A dryer-added fabric conditioning article comprising a rayon nonwoven fabric substrate (having a weight of 1.22 g per 99 sq. in. (approximately 639 $cm^2$)) and a fabric conditioning composition is prepared in the following manner.

A premixture is prepared by admixing 11.63 parts octadecyldimethylamine with about 20.59 parts $C_{16-18}$ fatty acid at 75° C. Then about 18.93 parts of particulate Complex 6, which is small enough so that all of the particles pass through a 40 mesh screen, is added with mixing to said premixture. Then about 20.20 parts sorbitan monostearate and 20.20 parts ditallowdimethylammonium methylsulfate are added with high shear mixing at about 75° C. After the addition is completed and a sufficient period of mixing time has elapsed, about 5.99 parts of Bentolite L particulate clay is added slowly while maintaining the high shear mixing action.

Finally about 2.46 parts of free Perfume C is added to complete the preparation of the fabric conditioning composition.

The flexible substrate, comprised of 70% 3-denier, 1-9/16 inch long (approximately 4 cm) rayon fibers and 30% polyvinyl acetate binder, is impregnated by coating one side of a continuous length of the substrate and contacting it with a rotating cylindrical member which serves to press the liquified mixture into the interstices of the substrate. The amount of fabric conditioning mixture applied is controlled by the flow rate of the mixture and/or the line speed of the substrate. The substrate is passed over several chilled tension rolls which help solidify the conditioning mixture. The substrate sheet is 9 inches wide (approximately 23 cm) and is perforated in lines at 11 inch intervals (approximately 28 cm) to provide detachable sheets. Each sheet is cut with a set of knives to provide three evenly spaced parallel slits averaging about 4 inches in length (approximately 10 cm). In this Example 10, the application rate is adjusted to apply about 2.52 g of coating mixture per sheet. Each sheet contains about 1.83 g of softener, about 0.15 g of clay, about 0.48 g of Complex 6, and about 0.062 g of free Perfume C.

| Components | Example 11 | Example 12 | Example 13 |
|---|---|---|---|
| Octadecyldimethylamine | 10.85 | 10.85 | 10.85 |
| $C_{16-18}$ fatty acid | 19.21 | 19.21 | 19.21 |
| DTDMAMS | 18.85 | 18.85 | 18.85 |
| Sorbitan monostearate | 18.85 | 18.85 | 18.85 |
| Clay | 4.50 | 4.50 | 4.50 |
| Complex 7 | 27.74 | — | — |
| Complex 8 | — | 27.74 | — |
| Complex 9 | — | — | 27.74 |
| Totals | 100.00 | 100.00 | 100.00 |
| Coating Wt. per Sheet (g) | 2.45 | 2.45 | 2.45 |

| Components | Example 14 | Example 15 | Example 16 |
|---|---|---|---|
| Octadecyldimethylamine | 10.85 | 10.85 | 10.85 |
| $C_{16-18}$ fatty acid | 19.21 | 19.21 | 19.21 |
| DTDMAMS | 18.85 | 18.85 | 18.85 |
| Sorbitan monostearate | 18.85 | 18.85 | 18.85 |
| Clay | 4.50 | 4.50 | 4.50 |
| Complex 10 | 27.74 | — | — |
| Complex 11 | — | 27.74 | — |
| Complex 12 | — | — | 27.74 |
| Totals | 100.00 | 100.00 | 100.00 |
| Coating Wt. per Sheet (g) | 2.45 | 2.45 | 2.45 |

| Components | Example 17 | Example 18 | Example 19 |
|---|---|---|---|
| Octadecyldimethylamine | 10.85 | 10.85 | 10.85 |
| $C_{16-18}$ fatty acid | 19.21 | 19.21 | 19.21 |
| DTDMAMS | 18.85 | 18.85 | 18.85 |
| Sorbitan monostearate | 18.85 | 18.85 | 18.85 |
| Clay | 4.50 | 4.50 | 4.50 |
| Complex 13 | 27.74 | — | — |
| Complex 14 | — | 27.74 | — |
| Complex 15 | — | — | 27.74 |
| Totals | 100.00 | 100.00 | 100.00 |
| Coating Wt. per Sheet (g) | 2.45 | 2.45 | 2.45 |

| Components | Example 20 | Example 21 |
|---|---|---|
| Octadecyldimethylamine | 10.85 | 20.54 |
| $C_{16-18}$ fatty acid | 19.21 | 18.81 |
| DTDMAMS | 18.85 | 16.46 |
| Sorbitan monostearate | 18.85 | 16.46 |
| Clay | 4.50 | 5.91 |
| Complex 16 | 27.74 | — |
| Complex 17 | — | 21.82 |
| Totals | 100.00 | 100.00 |
| Coating Wt. per Sheet (g) | 2.45 | |

EXAMPLES 11-21

Fabric conditioning sheets of Examples 11 to 20 are prepared by the same procedure as that of Example 7 with the exception that no extra free perfume is added. The target coating weight is 2.45 g per sheet. The target coating weight for Example 21 is 2.2 g per sheet.

Fabrics treated with any of the above sheets in the tumble dryer will emit extra fragrance order when the fabrics are rewetted with water or perspiration.

Example 22

A dryer-added fabric conditioning article of manufacture comprising a rayon nonwoven fabric substrate (having a weight of 1.22 gm per 99 sq. in.) and a fabric conditioning composition is prepared in the following manner.

Preparation of the Fabric Treatment Mixture

A blend of about 21.60 parts of ditallowdimethylammonium methyl sulfate (DTDMAMS) (sold by Sherex Chemical Co.) and about 2.40 parts of sorbitan monostearate (sold by Mazer Chemicals, Inc.) is melted and mixed well at 80.C. To this mixture, about 40 parts of soil release agent mixture containing about 30 parts of the Soil Release Agent I and about 10 parts of fatty acid, at 85.C is added with high-shear mixing to finely disperse the soil release agent mixture. The temperature of the mixture is kept between 70°-80° C. using a water bath. After the addition is completed, about 6 parts of Bentolite L particulate clay (sold by Southern Clay Products), and about 15 parts of the Complex 7 between Perfume A and β-CD are added sequentially and slowly while maintaining the high-shear mixing action to make the fabric treatment mixture.

Preparation of Fabric Conditioning Sheets

The fabric treatment mixture is applied to preweighed nonwoven substrate sheets of a 9 inch × 11 inch (approximately 23×28 cm) dimension. The substrate sheets are comprised of 70% 3-denier, 1-9/16 inch (approximately 4 cm) long rayon fibers with 30% polyvinyl acetate binder. A small amount of the fabric treatment mixture is placed on a heated metal plate with a spatula and then is spread evenly with a small metal roller. A nonwoven sheet is placed on it to absorb the fabric treatment mixture. The sheet is then removed from the heated metal plate and allowed to cool to room temperature so that the fabric treatment mixture can solidify. The sheet is weighed to determine the amount of fabric treatment mixture on the sheet. The target amount is 3.0 g per sheet. Each sheet contains about 0.78 g of Soil Release Agent I and about 0.39 g of Complex 7 (Perfume-A/β-CD complex). If the weight is under the target weight, the sheet is placed on the heated metal plate and more fabric treatment mixture is added. If the weight is in excess of the target weight, the sheet is placed back on the heated metal plate to remelt the fabric treatment mixture and remove some of the excess.

EXAMPLE 23

A blend of about 18.36 parts of octadecyldimethylamine (Ethyl Corp.) and about 15.64 parts of $C_{16}$-$C_{18}$ fatty acid (Emery Industries, Inc.) is melted at 80 C, and a blend of about 14.71 parts of DTDMAMS (Sherex Chemical Co.) and about 14.71 parts of sorbitan monostearate (Mazer Chemicals, Inc.) is melted at 80° C. The two blends are then mixed together to form the softener component.

Next, a soil release agent mixture, containing about 15 parts of the Soil Release Agent I and about 2.5 parts of ethylene glycol (Fisher Scientific) is added with high-shear mixing while the temperature of the softener is kept between 70°–80° C. using a water bath, until all of the soil release agent mixture has been mixed into the softener matrix.

Then, the calcium bentonite clay (about 6 parts, Bentolite L from Southern Clay Co.), followed by about 15 parts of the Complex 8 are added with high-shear mixing. Finally, 2 parts of free Perfume A are added with mixing to make the fabric treatment mixture.

The preparation of the fabric conditioning sheets is similar to that in Example 22. The target coating weight is 3.1 g per sheet. Each sheet contains about 0.45 g of Soil Release Agent I, about 0.459 of Complex 8 (complex of the volatile Perfume B), and about 0.06 g of free Substantive Perfume A.

EXAMPLES 24 AND 25

The preparations of the fabric treatment mixtures and fabric conditioning sheets of Examples 24 and 25 are similar to that in Example 22. The target coating weight is 2.84 g per sheet. Each sheet contains about 0.64 g of soil release agent, about 0.50 g of Perfume Complex, and about 0.05 g of free perfume.

| Components | Example 24 | Example 25 |
|---|---|---|
| Octadecyldimethylamine | 15.06 | 15.06 |
| $C_{16-18}$ Fatty Acid | 13.79 | 13.79 |
| Sorbitan Monostearate | 12.07 | 12.07 |
| DTDMAMS | 12.07 | 12.07 |
| Calcium Bentonite Clay[a] | 4.97 | 4.97 |
| Complex 15 | 17.64 | — |
| Complex 16 | — | 17.64 |
| Perfume C | 1.76 | 1.76 |
| Milease TL | 22.64 | 22.64 |
| Totals | 100.00 | 100.00 |
| Coating Wt. per Sheet g | 2.84 | 2.84 |

[a]Bentolite L sold by Southern Clay Products.

EXAMPLES OF DETERGENT-COMPATIBLE PARTICLES

EXAMPLES 26 AND 27

| Softener Core Particles | | |
|---|---|---|
| Components | Example 26 | Example 27 |
| Ditallowdimethylammonium methylsulfate (DTDMAMS) | 38.51 | 38.51 |
| Cetyl Alcohol | 19.17 | 19.17 |
| Sorbitan Monostearate | 19.17 | 19.17 |
| Complex 3 | 23.15 | 20.15 |
| Colcium Bentonite Clay | — | 3.00 |
| Totals | 100.00 | 100.00 |

The DTDMAMS, cetyl alcohol and sorbitan monostearate are blended together in a PVM 40 Ross mixer (charles Ross & Sons Company, Hauppauge, New York 11788) at about 71° C. The molten "triblend" is then mixed for one hour. At the end of one hour, the temperature is raised to 79°–85° C. under vacuum (about 330–430 mm Hg). When the temperature has stabilized in this range, the Ross anchor and disperser are turned on and, in separate batches, the Complex 3 and, for Example 27, the clay are added, the mixture is blended for 5 minutes and then sheared with the Ross colloid mixer for 10 minutes. The softener composition is then poured into trays and cooled overnight at about 4° C. Particles are formed by cooling and then milling in a Fitzmill, Model DA506 (The Fitzpatrick Company, Elmhurst, Illinois 60126) at 4740 rpm's through a 4 mesh screen. The particles are then sized through 11 on 26 (U.S. Standard screens, (0.6–1.7 mm) particle size).

The particles are then coated with a 10% solution of Ethocel in methanol. The coating is applied in an 18 inch Wurster Coater (Coating Place, Inc., P.O. Box 248, Verona, Wisconsin 53593). The ethyl cellulose used is Ethocel Std. IO (Dow Chemical Co., Midland, Michigan 48640), which has an Ubbelohde viscosity of 9.0–11.0, measured at 25° C. as a 5% solution in 80% toluene/20% ethanol.

The following conditions are used to apply the cellulose-based coating:

| | |
|---|---|
| Fluidizing Air | 15.8 Cu. M/min. at 40.5° C. |
| Atomizing Air Volume | 0.37 Cu. M/min. |
| Atomizing Air Rate | 5624 g/sq. cm. |
| Inlet Air Temperature | 38° C.–43° C. |
| Outlet Air Temperature | 30° C.–32° C. |
| Pump Rate | 0.2 Kg/min. |
| Nozzle Size | CPI-18-A74* |
| Partition Gap | 216 mm × 267 mm |
| Partition Size | 19 mm |
| Run Time | 55 min. |

*Available from Coating Place, Inc.

The amount of coating applied to the particles is about 3% by weight of the total coated particle weight. When the coating is completed, the softener particles are resized through 11 on 26 mesh U.S. Standard screens and are then ready for use "as is" or for blending into detergent granules.

EXAMPLE 28

A detergent/softener composition is prepared by mixing about 5.2 parts of the coated softener particles of Examples 26 with 94.8 parts of the following granular detergent composition:

| Ingredient | Parts |
|---|---|
| Na $C_{13}$ linear alkyl benzene sulfonate | 9.5 |
| Na $C_{14}$–$C_{15}$ fatty alcohol sulfate | 9.5 |
| Ethoxylated $C_{12}$–$C_{13}$ fatty alcohol | 1.9 |
| $Na_2SO_4$ | 11.1 |
| Sodium silicate (1.6 r) | 6.5 |
| Polyethylene glycol (M.W. 8,000) | 0.7 |
| Polyacrylic acid (M.W. 1,200) | 0.9 |
| Sodium tripolyphosphate | 31.0 |
| Sodium pyrophosphate | 7.5 |
| $Na_2CO_3$ | 10.2 |
| Optical brightener | 0.2 |
| Protease enzyme (Alcalase) | 0.7 |
| Moisture | 9.3 |
| Miscellaneous | 1.0 |
| Total | 100.0 |

EXAMPLE 29

Alternate granular detergent/softener compositions are prepared by mixing about 5.2 parts of the coated softener of Example 27 with about 94.8 parts of the following granular detergent composition:

| Ingredient | Parts |
|---|---|
| Na $C_{13}$ linear alkyl benzene sulfonate | 11.5 |

-continued

| Ingredient | Parts |
| --- | --- |
| Na $C_{14}$-$C_{15}$ fatty alcohol sulfate | 11.5 |
| Ethoxylated $C_{12}$-$C_{13}$ fatty alcohol | 1.9 |
| $Na_2SO_4$ | 14.0 |
| Sodium silicate (1.6 r) | 2.3 |
| Polyethylene glycol (M.W. 8,000) | 1.8 |
| Polyacrylic acid (M.W. 1,200) | 3.5 |
| Hydrated Zeolite A (~2 microns) | 28.9 |
| $Na_2CO_3$ | 17.0 |
| Optical brightener | 0.2 |
| Protease enzyme (Alcalase) | 0.6 |
| Moisture and Miscellaneous | 7.0 |
| Total | 100.2 |

EXAMPLE 30

Four laundry loads (Loads A, B, C, and D) containing mixed fabric types are washed with the unscented TIDE ® detergent. The wet laundry loads are transferred to four electric tumble dryers for drying. About 1 gram of Complex 2 is sprinkled onto each wet laundry load in the drying step. Load A is sprinkled with Complex 2 right at the beginning of the 50-minute drying cycle. Loads B, C, and D are treated at 15 minutes, 25 minutes, and 35 minutes, respectively, into the drying cycle. The resulting dry fabrics have some light perfume odor, with fabrics of Load A having more odor than the other loads. When the fabrics of Loads A, B, C, and D are rewetted, a noticeable stronger perfume odor is obtained.

We claim:

1. Solid, laundry dryer-activated, fabric conditioning composition consisting essentially of from about 30% to about 99% of fabric softening agent selected from the group consisting of: cationic fabric softener; nonionic fabric softener; and mixtures thereof, and from about 0.5% to about 60% of perfume/cyclodextrin complex, said composition being capable of improving the condition of fabrics being dried in a alundry dryer and attaching an effective amount of said perfume/cyclodextrin complex to said fabrics in said laundry dryer at said laundry dryer's operating temperatures, whereby said fabrics, when dry, exhibit substantial odor of said perfume upon rewetting.

2. The composition of claim 1 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin is capable of forming inclusion complexe with perfume ingredients.

3. The composition of claim 2 wherein at least a major portion of said cyclodextrin is selected from the group consisting of beta-cyclodextrin; gamma-cyclodextrin; and mixtures thereof.

4. The composition of claim 3 wherein at least a major portion of said cyclodextrin is beta-cyclodextrin.

5. The composition of claim 4 wherein at least a major portion of said perfume is selected from the group consisting of: highly volatile perfume; moderately volatile perfume; and mixtures thereof.

6. The composition of claim 5 wherein at least a major portion of said perfume is highly volatile perfume.

7. The composition of claim 1 wherein at least a major portion of said perfume is selected from the group consisting of: highly volatile perfume; moderately volatile perfume; and mixtures thereof.

8. The composition of claim 7 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin is capable of forming inclusion complexes with perfume ingredients.

9. The composition of claim 7 wherein at least a maJor portion of said cyclodextrin comprises cyclodextrin selected from the group consisting of beta-cyclodextrin; gamma-cyclodextrin; and mixtures thereof.

10. The composition of claim 1 wherein said fabric conditioning composition comprises at least an effective amount of cationic fabric softening agent.

11. The composition of claim 10 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin is capable of forming inclusion complexes with perfume ingredients.

12. The composition of claim 11 wherein at least a major portion of said cyclodextrin is selected from the group consisting of beta-cyclodextrin; gamma-cyclodextrin; and mixtures thereof.

13. The composition of claim 12 wherein at least a major portion of said perfume is selected from the group consisting of: highly volatile perfume; moderately volatile perfume; and mixtures thereof.

14. The composition of claim 10 wherein at least a major portion of said perfume is selected from the group consisting of: highly volatile perfume; moderately volatile perfume; and mixtures thereof.

15. The composition of claim 10 wherein said fabric conditioning composition additionally comprises an effective amount of nonionic softening agent.

16. The composition of claim 15 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin in capable of forming inclusion complexes with perfume ingredients.

17. The composition of claim 16 wherein at least a major portion of said cyclodextrin is selected from the group consisting of beta-cyclodextrin; gamma-cyclodextrin; and mixtures thereof.

18. The composition of claim 17 wherein at least a major portion of said perfume is selected from the group consisting of: highly volatile perfume; moderately volatile perfume; and mixtures thereof.

19. The composition of claim 1 wherein at least a major portion of said perfume/cyclodextrin complex has a particle size greater than about 10 microns.

20. The composition of claim 19 wherein said particle size is from about 10 microns to about 250 microns.

21. The composition of claim 1 wherein at least a major portion of said perfume/cyclodextrin complex has a particle size of less than about 10 microns.

22. The composition of claim 1 wherein said perfume/cyclodextrin complex has particles ranging in size between about 0.01 micron to about 1,000 microns with substantial amounts both below and above 10 microns.

23. An article of manufacture consisting essentially of:
   I. a fabric conditioning composition comprising:
      i. from about 30% to about 99% of fabric softening agent selected from the group consisting of: cationic fabric softener; nonionic fabric softener; and mixtures thereof; and
      ii. from about 0.5% to about 60% of perfume/cyclodextrin complex; and
   II. a dispensing means which provides for release of an effective amount of said composition to fabrics in a laundry dryer at said laundry dryer's operating temperatures whereby an effective amount of said perfume/cyclodextrin complex is attached to said fabrics, when they are dry, so that said fabrics exhibit substantial odor of said perfume upon rewetting.

24. The article of manufacture of claim 23 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin is capable of forming inclusion complexes with perfume ingredients.

25. The article of manufacture of claim 24 wherein at least a major portion of said cyclodextrin is selected from the group consisting of beta-cyclodextrin; gamma-cyclodextrin; and mixtures thereof.

26. The article of manufacture of claim 24 wherein at least a major portion of said cyclodextrin is beta-cyclodextrin.

27. The article of manufacture of claim 26 wherein at least a major portion of said perfume is selected from the group consisting of: highly volatile perfume; moderately volatile perfume; and mixtures thereof.

28. The article of manufacture of claim 27 wherein at least a major portion of said perfume is highly volatile perfume.

29. The article of manufacture of claim 23 wherein at least a major portion of said perfume is selected from the group consisting of: highly volatile perfume; moderately volatile perfume; and mixtures thereof.

30. The article of manufacture of claim 29 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin is capable of forming inclusion complexes with perfume ingredients.

31. The article of manufacture of claim 30 wherein at least a major portion of said cyclodextrin comprises a cyclodextrin selected from the group consisting of beta-cyclodextrin; gamma-cyclodextrin; and mixtures thereof.

32. A detergent-compatible, laundry dryer-activated fabric conditioning composition in particulate form consisting essentially of:
   I. from about 30% to about 99% of fabric softening agent selected from the group consisting of; cationic fabric softener; nonionic fabric softener; and mixtures thereof; and
   II. from about 0.5% to about 60% of perfume/cyclodextrin complex, said composition being capable of attaching an effective amount of said perfume/cyclodextrin complex to fabrics in a laundry dryer at said laundry dryer's operating temperatures, whereby said fabrics, when they are dry, exhibit substantial odor of said perfume upon rewetting.

33. The composition of claim 32 wherein said cyclodextrin is selected from the group consisting of:. unsubstituted cyclodextrins containing from about six to about twelve glucose units; derivatives of said unsubstituted cyclodextrins; and mixtures thereof, and wherein said cyclodextrin is capable of forming inclusion complexes with perfume ingredients 34. The composition of claim 33 wherein at least a major portion of said perfume is selected from the group consisting of: highly volatile perfume; moderately volatile perfume; and mixtures thereof.

35. A detergent composition comprising an effective amount of the composition of claim 32.

* * * * *